(12) United States Patent
Idegami et al.

(10) Patent No.: US 8,927,219 B2
(45) Date of Patent: Jan. 6, 2015

(54) METHOD FOR EVALUATION OF QUALITY OF BLOOD SAMPLE

(75) Inventors: Koutarou Idegami, Kanazawa (JP); Takashi Yoneda, Kanazawa (JP); Yuzuru Takamura, Nomi (JP)

(73) Assignees: Japan Advanced Institute of Science and Technology, Nomi-shi (JP); Kanazawa University, Kanazawa-shi (JP)

( * ) Notice: Subject to any disclaimer, the term of this patent is extended or adjusted under 35 U.S.C. 154(b) by 539 days.

(21) Appl. No.: 12/744,064

(22) PCT Filed: Nov. 25, 2008

(86) PCT No.: PCT/JP2008/071346
§ 371 (c)(1),
(2), (4) Date: Oct. 6, 2010

(87) PCT Pub. No.: WO2009/066787
PCT Pub. Date: May 28, 2009

(65) Prior Publication Data
US 2011/0244476 A1 Oct. 6, 2011

(30) Foreign Application Priority Data
Nov. 22, 2007 (JP) .................. 2007-303112

(51) Int. Cl.
*G01N 33/53* (2006.01)
*G01N 33/74* (2006.01)
*G01N 33/558* (2006.01)
*G01N 33/94* (2006.01)

(52) U.S. Cl.
CPC ...... *G01N 33/546366* (2013.01); *G01N 33/558* (2013.01); *G01N 33/9493* (2013.01)
USPC ........................................... 435/7.1; 436/501

(58) Field of Classification Search
CPC .......... G01N 33/54366; G01N 33/558; G01N 33/9493; G01N 33/98; G01N 33/54306; G01N 33/5438; G01N 33/743; C12Q 1/26; C12Q 1/28; C12Q 1/005; Y10S 436/817
See application file for complete search history.

(56) References Cited

U.S. PATENT DOCUMENTS 4,208,479 A * 6/1980 Zuk et al. .................. 435/7.9
6,383,766 B1 * 5/2002 Warren et al. .............. 435/7.93

FOREIGN PATENT DOCUMENTS

| JP | 7 325085 | 12/1995 |
| JP | 2005 31029 | 2/2005 |
| JP | 2006-170658 A | 6/2006 |
| JP | 2007 169209 | 7/2007 |

OTHER PUBLICATIONS

Leung et al., J. Immunol. Methods, 2003; vol. 281 pp. 109-118.*
Fitzgerald catalog page retrieved URL: www.fitzgerald-fii.com/cortisol-3-bsa-80-ic20.html, accessed on Mar. 20, 2013.*
Nara et al., Analytical Biochemistry 2008; vol. 373, pp. 18-25, published on line Nov. 4, 2007.*
Milipore Guide 2002;retrieved from http://www.millipore.com/publications.nsf/a73664f9f981af8c852569b9005b4eee/348ee7096d93729b85256bf40066a40d/$FILE/tb500en00.pdf.*
Combined Chinese Office Action and Search Report issued Nov. 15, 2012 in Chinese Patent Application No. 200880125040.1 (with English-language translation).
Omura, M., "Diagnosis of Special Types of Primary Aldosteronism—Usefulness of Adrenal Venous Sampling—", Saishin Igaku Company, vol. 59, No. 10, pp. 2286-2291, (2004) (with partial English translation).
Mengozzi, G. et al., "Rapid Cortisol Assay During Adrenal Vein Sampling in Patients With Primary Aldosteronism", Clinical Chemistry, vol. 53, No. 11, pp. 1968-1971 (2007).

* cited by examiner

*Primary Examiner* — Shafiqul Haq
*Assistant Examiner* — Carmencita M Belei
(74) *Attorney, Agent, or Firm* — Oblon, Spivak, McClelland, Maier & Neustadt, L.L.P.

(57) ABSTRACT

A method for evaluating the quality of a blood sample, comprising the steps of: mixing labeled anti-cortisol antibodies with a blood sample to be subjected, to conduct the antigen-antibody reaction of the labeled anti-cortisol antibody with cortisol contained in the blood sample, developing a mixture obtained in the above step on an immunochromatographic test strip having a substrate on which cortisol is immobilized to cause the antigen-antibody reaction of the labeled anti-cortisol antibodies which are free in the mixture with the cortisol immobilized on the substrate, thereby bonding the antibody to the cortisol, determining the amount of the labeled anti-cortisol antibodies bonded to the cortisol in the above step, and evaluating whether or not the blood sample has a quality suitable for suprarenal vein sampling test on the basis of the amount of the labeled anti-cortisol antibodies determined in the above step.

5 Claims, 9 Drawing Sheets

METHOD FOR EVALUATION OF QUALITY OF BLOOD SAMPLE

CROSS-REFERENCE TO RELATED APPLICATIONS

This application is a National Stage of PCT/JP08/071346 filed Nov. 25, 2008 and claims the benefit of JP 2007-303112 filed Nov. 22, 2007.

TECHNICAL FIELD

The present invention relates to a method for evaluating the quality of a blood sample. More particularly, the present invention relates to a method for evaluating the quality of a blood sample, an immunochromatographic test strip used therefor, and a kit for evaluating the quality of a blood sample, which contains the immunochromatographic test strip.

BACKGROUND ART

A blood sample is used for, for example, diagnosis of the state of a subject, judgment for selection of the optimal treatment for disease and the like. However, in some cases, the blood sample which sufficiently reflects the state and disease of a subject cannot be obtained depending on the blood-sampling position. In this case, diagnosis of the state of a subject and judgment for selection of the optimal treatment for disease cannot be accurately carried out.

As a disease for which judgment of the state of the disease or judgment for selection of a treatment method is carried out by using a blood sample, there have been known, for instance, aldosteronism. Aldosteronism is disease which causes hypersecretion of an aldosterone in the suprarenal cortex itself. Aldosteronism is classified roughly into idiopathic hyperaldosteronism and glucocorticoid-remediable hyperaldosteronism which are caused by hyperplasia, and aldosterone-producing adenoma which is caused by adenoma. A treatment method based on drug dosing has been adopted for aldosteronism caused by hyperplasia. In addition, a treatment method based on surgical extirpation has been adopted for aldosterone-producing adenoma.

When a treatment method is selected in accordance with the pattern of disease of the aldosteronism, an adrenal vein sampling test has been conducted (see, for instance, non-patent document 1, non-patent document 2 and the like). In the adrenal vein sampling test, a catheter is inserted into right and left suprarenal veins, about 5 mL of a blood sample is collected, and thereafter the amount of an aldosterone in the blood sample is determined.

However, in the adrenal vein sampling test, since the inside diameter of the suprarenal vein into which a catheter is inserted and the diameter of catheter used is small, blood sampling might be difficult. Moreover, bloods derived from various veins are flown into the suprarenal vein. Therefore, the aldosterone contained in the blood sample obtained by blood sampling might be diluted with the bloods. In this case, the adrenal vein sampling test might not be able to be accurately conducted.

The aptitude of the blood sample used for the adrenal vein sampling test is evaluated on the basis of cortisol concentration in the blood sample. Since a large-scale device is usually necessary for the determination of cortisol concentration, the cortisol concentration could not be easily determined on the surgical site and the like. Therefore, in general, since it is necessary to perform the determination of cortisol concentration in an external institution such as a test agency or a test post, a long term of around several days to one week is required for obtaining the result of the determination.

On the other hand, a substance to be tested, which is contained in a test sample has been detected by an immunochromatography and the like. In the immunochromatography, a liquid dispersion of labeled antibodies obtained by immobilizing antibodies onto the metallic microparticle has been used (see, for instance, patent document 1 and the like).

Patent document 1: Japanese Unexamined Patent Publication No. 2007-169209

Non-patent document 1: Masao Omura, "Diagnosis of specific subtype of primary aldosteronism—signification of adrenal vein sampling", *Saishin Igaku* (Current medicine), Saishin Igaku company, 2004, Vol. 59, No. 10, p. 2286-2291

Non-patent document 2: Giulio Mengozzi and other 7 authors, "Rapid Cortisol Assay during Adrenal Vein Sampling in Patients with Primary Aldosteronism", *Clinical Chemistry*, November, 2007, Vol. 53, No. 11, p. 1968-1971

DISCLOSURE OF THE INVENTION

Problems to be Solved by the Invention

An object of the present invention is to provide a method for evaluating the quality of a blood sample, which can evaluate the quality of a blood sample quickly and easily by using a small amount of a blood sample. Another object of the present invention is to provide an immunochromatographic test strip and a kit for evaluating the quality of a blood sample which can be suitably used for evaluating quickly and easily the quality of a blood sample by using a small amount of a blood sample.

Means for Solving the Problem

The present invention relates to:

(1) a method for evaluating the quality of a blood sample, comprising the steps of:

(a) mixing labeled anti-cortisol antibodies with a blood sample to be subjected, to conduct the antigen-antibody reaction of the labeled anti-cortisol antibodies with cortisol contained in the blood sample, (b) developing the resulting mixture in the step (a) on an immunochromatographic test strip having a substrate on which cortisol is immobilized, to cause the antigen-antibody reaction of the labeled anti-cortisol antibodies which are free in the mixture with the cortisol immobilized on the substrate, thereby bonding the antibodies to the cortisol, (c) determining the amount of the labeled anti-cortisol antibodies bonded to the cortisol in the step (b), and (d) evaluating whether or not the blood sample has a quality suitable for suprarenal vein sampling test on the basis of the amount of the labeled anti-cortisol antibodies determined in the step (c);

(2) a method for evaluating the quality of a blood sample, comprising the steps of:

(A) using an immunochromatographic test strip having a labeled antibody phase provided on one end of a substrate and cortisol immobilized on the other end of the substrate, wherein the labeled antibody phase holds labeled anti-cortisol antibodies so that the labeled anti-cortisol antibodies are detached by contacting with the blood sample to be tested, thereby developing a given amount of the blood sample to be tested from the end of the labeled antibody phase of the immunochromatographic test strip, to cause the antigen-antibody reaction of the labeled anti-cortisol antibodies with cortisol contained in the blood sample, and thereafter subjecting free forms of labeled anti-cortisol antibodies after the antigen-antibody reaction to another antigen-antibody reaction with cortisol immobilized on the substrate, thereby bonding the antibodies to the cortisol immobilized on the substrate, (B) determining the amount of the labeled anti-cortisol antibodies bonded to the cortisol immobilized on the substrate in the step (A), and (C) evaluating whether or not the blood sample has a quality suitable for suprarenal vein sampling test on the basis of the amount of the labeled anti-cortisol antibodies determined in the step (B);

(3) an immunochromatographic test strip for use in a method for evaluating the quality of a blood sample of the above item (1), wherein cortisol is immobilized on the strip via a linker; and (4) an immunochromatographic test strip for use in a method for evaluating the quality of a blood sample of the above item (2), wherein the labeled antibody phase which holds labeled anti-cortisol antibodies so that the labeled anti-cortisol antibodies are detached by contacting with the blood sample to be tested is provided on one end of a substrate, and cortisol is immobilized on the other end of the substrate via a linker; and (5) a kit for evaluating the quality of a blood sample, comprising the above immunochromatographic test strip.

Advantageous Effects of the Invention

According to the method for evaluating the quality of a blood sample of the present invention, there can be evaluated the quality of the blood sample quickly and easily by using a small amount of a blood sample. The immunochromatographic test strip and the kit for evaluating the quality of a blood sample of the present invention can be suitably used for quickly and easily evaluating the quality of a blood sample by using a small amount of the blood sample.

BEST MODE FOR CARRYING OUT THE INVENTION

Figure 1:
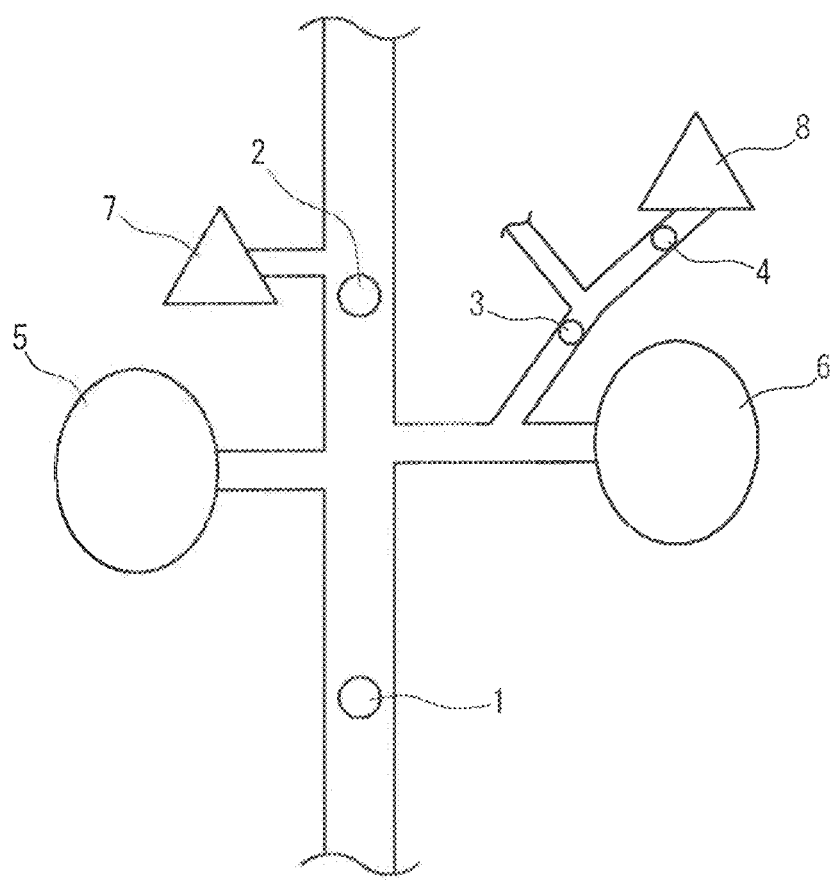
FIG. 1 is a schematic explanation view of the sampling position where a blood sample is collected in Examples 2 and 3 according to the present invention.

The method for evaluating the quality of a blood sample of the present invention includes the steps of:

(a) mixing labeled anti-cortisol antibodies with a blood sample to be subjected, to conduct the antigen-antibody reaction of the labeled anti-cortisol antibodies with cortisol contained in the blood sample, (b) developing the resulting mixture in the step (a) on an immunochromatographic test strip having a substrate on which cortisol is immobilized, to cause the antigen-antibody reaction of the labeled anti-cortisol antibodies which are free in the mixture with the cortisol immobilized on the substrate, thereby bonding the antibody to the cortisol, (c) determining the amount of the labeled anti-cortisol antibodies bonded to the cortisol in the step (b), and (d) evaluating whether or not the blood sample has a quality suitable for suprarenal vein sampling test on the basis of the amount of the labeled anti-cortisol antibodies determined in the step (c). Hereinafter, this method for evaluating the quality is referred to as "evaluation method 1".

In the step (a), a blood sample to be tested is mixed with a labeled anti-cortisol antibody, to conduct the antigen-antibody reaction of cortisol with the labeled anti-cortisol antibody contained in the blood sample.

In the mixture obtained in the step (a), a complex is formed by the antigen-antibody reaction of cortisol contained in the blood sample with the labeled anti-cortisol antibodies. In addition, free forms of labeled anti-cortisol antibodies remain depending on the amount of cortisol contained in the blood sample. Usually, the amount of the free forms of labeled anti-cortisol antibodies which do not form a complex relatively decreases in accordance with the increase of the amount of the cortisol contained in the blood sample.

The blood sample to be tested includes, for instance, plasma, serum, whole blood and the like. Among the blood samples to be tested, plasma is preferable from the viewpoint of association of cortisol with the labeled anti-cortisol antibody contained in the blood sample more efficiently to form a complex.

The shorter the distance from the vein to the adrenal gland is, the more the amount of cortisol contained in the venous blood increases. Therefore, the amount of cortisol contained in the blood sample collected from suprarenal vein is larger than that of cortisol contained in the peripheral blood in the same volume as the blood sample. The cortisol content in the peripheral blood may increase from that of the peripheral blood under a normal condition due to a stress on the individual or the timing of sampling of the blood sample. Therefore, it is preferable that the blood sample to be tested is a blood sample of an individual under a normal condition.

The labeled anti-cortisol antibody is an antibody which is obtained by labeling antibody raised against cortisol (hereinafter referred to as "anti-cortisol antibody") with a labeling substance.

The anti-cortisol antibody can be a monoclonal antibody raised against cortisol or a polyclonal antibody raised against cortisol. The monoclonal antibody and polyclonal antibody which are raised against cortisol can be obtained according to, for instance, a method described in "Current Protocols in Immunology" edited by John E. Coligan, published by John Wiley & Sons, Inc, issued in 1992 and the like.

More specifically, the monoclonal antibody raised against cortisol can be obtained by, for instance, immunizing with cortisol an animal such as a rabbit or a goat, collecting a splenocyte from the resulting immunized animal, fusing the resulting splenocyte to a myeloma cell, to give a hybridoma, culturing the hybridoma and thereafter purifying a monoclonal antibody contained in the culture supernatant of the hybridoma. The polyclonal antibody raised against cortisol can be obtained by, for instance, immunizing with cortisol an animal such as a rabbit or a goat, collecting a serum from the resulting immunized animal and thereafter purifying the polyclonal antibody contained in the serum.

The labeling substance includes, for instance, a colloidal metal particle, an enzyme, a fluorescent substance and the like. Among them, the colloidal metal particle is preferable from the viewpoint of easiness of the detection operation and excellent visibility.

The colloidal metal particle includes, for instance, a colloidal gold particle, a colloidal silver particle, a colloidal platinum particle, a colloidal composite metal particle thereof, a colloidal selenium particle and the like. These can be used alone or in admixture of not less than two kinds. Among them, the colloidal gold particle is preferable from the viewpoint of excellent stability and excellent visibility.

The quantitative determination of the colloidal metal particle can be carried out by, for instance, determining the absorbance of the colloidal metal particle at a wavelength of 520 nm.

The enzyme includes, for instance, a peroxidase, an alkaline phosphatase, a glucose oxidase and the like. These can be used alone or in admixture of not less than two kinds. The quantitative determination of the enzyme can be carried out by a method of determining a specific activity of the enzyme and the like.

The fluorescent substance includes, for instance, fluorescein isothiocyanate, tetramethylrhodamine isothiocyanate and the like. These can be used alone or in admixture of not less than two kinds. The quantitative determination of the fluorescent substance can be carried out by, for instance, a method of determining a fluorescent intensity of the fluorescent substance and the like.

The labeled anti-cortisol antibodies can be dissolved in, for instance, phosphate buffer, Tris buffer and the like as occasion demands.

It has been generally considered that it becomes an index of being a blood sample suitable for suprarenal-vein sampling test that the cortisol concentration in the blood sample is twice or more times greater than the concentration of cortisol contained in the peripheral blood. Therefore, it is preferable that the amount of the labeled anti-cortisol antibodies which are to be mixed with the blood sample to be tested is twice or more times as high as the molar amount of the cortisol contained in the peripheral blood. The reason why the peripheral blood is selected is that the peripheral blood is considered to be suitable for use as a standard, since the content of cortisol is the lowest in the peripheral blood.

The shorter the distance from the vein to the adrenal gland is, the more the amount of cortisol contained in the venous blood increases. Therefore, the amount of cortisol contained in the blood sample collected from suprarenal vein is larger than that of cortisol contained in a blood sample taken out from inferior vena cava (hereinafter referred to as "postcaval venous blood").

There can be visually evaluated whether or not a sample is a blood sample collected from the suprarenal vein, by the coloring of the labeling substance of the labeled anti-cortisol antibodies which bond to cortisol immobilized on a substrate of an immunochromatographic test strip. Therefore, in the step (a), it is preferable to use as the labeled anti-cortisol antibodies the labeled anti-cortisol antibodies each of which molar amount is greater than that of cortisol contained in, for instance, the postcaval venous blood. The upper limit of the molar amount of the labeled anti-cortisol antibodies to that of the blood sample to be tested can be appropriately controlled taking the cost required for the labeled anti-cortisol antibodies used in the step (a) into consideration.

In the step (a), the blood sample to be tested can be previously mixed with a washing liquid when the labeled anti-cortisol antibodies are mixed with the blood sample to be tested from the viewpoint of shortening the time required for the operation.

The washing liquid can be a liquid having a property for preventing the material from the nonspecific adsorption to the immunochromatographic test strip. The washing liquid includes, for instance, a neutral buffer containing a blocking reagent such as bovine serum albumin, casein, sericin, gelatin, 2-methacryloyloxyethyl phosphorylcholine polymer, polyvinylpyrrolidone or polyvinyl alcohol, and a surfactant such as a surfactant of Tween (registered trademark) series, a surfactant of Pluronic (registered trademark) series or a surfactant of Triton (registered trademark) X series. The amount of the washing liquid can be the amount sufficient for developing the mixture of the labeled anti-cortisol antibodies and the blood sample on the immunochromatographic test strip.

In the step (a), it is preferable to mix the labeled anti-cortisol antibodies with the blood sample while irradiating ultrasonic waves thereto from the viewpoint of shortening the time required for operation and accurately detecting a complex of the labeled anti-cortisol antibody and cortisol contained in the blood sample. The time is varied depending on the frequency of ultrasonic waves and the like. Therefore, the time required for mixing the labeled anti-cortisol antibodies with the blood sample while irradiating ultrasonic waves thereto cannot be indiscriminately determined. Usually, the time required for dispersing the labeled anti-cortisol antibodies and the blood sample uniformly can be selected.

In the step (a), the blood sample to be tested can be used as it is or after appropriately diluting with a solvent depending on the detection sensitivity of the immunochromatographic test strip used in the step (b), and the like.

In the step (a), the blood sample to be tested can be used as it is without diluting the blood sample, when the cortisol concentration in the peripheral blood of the individual is a given standard concentration. When the labeled anti-cortisol antibodies are mixed with the blood sample to be tested, the number of the labeled anti-cortisol antibodies per 10 μL of the blood sample is preferably not less than $3 \times 10^8$ from the viewpoint of high-sensitive determination of the amount of cortisol contained in the blood sample, and preferably not more than $9 \times 10^8$ from the viewpoint of reduction in the cost required for the labeled anti-cortisol antibody used in the step (a). When the colloidal gold-labeled anti-cortisol antibody solution is used as a labeled anti-cortisol antibody, the amount of the colloidal gold-labeled anti-cortisol antibody solution of which absorbance at a wavelength of 520 nm is 1 to 10 abs is 1 to 15 μL per 30 μL of the blood sample to be tested. The amount can be adjusted so that the product of the absorbance multiplied by the amount of the colloidal gold-labeled anti-cortisol antibody solution is 10 to 90 abs·µL.

In the step (a), when the cortisol concentration in the peripheral blood of the individual is expected to vary widely, at least two kinds of the labeled anti-cortisol antibodies per 10 µL of the blood sample in the case where the blood sample to be tested is used as it is without dilution are preferable, from the viewpoint of easy determination of the amount of the cortisol contained in the blood sample. The number of the labeled anti-cortisol antibodies per 10 µL of the blood sample is preferably $3 \times 10^8$ or more from the viewpoint of high-sensitive determination of the amount of cortisol contained in the blood sample, and preferably $2.4 \times 10^9$ or less from the viewpoint of reduction in the cost required for the labeled anti-cortisol antibodies used in the step (a).

In addition, from the viewpoint of determination of the amount of cortisol in easy operation and in a low cost, it is more preferable that the postcaval venous blood is used in place of the blood sample in the step (a), to select from the labeled anti-cortisol antibodies having at least two different numbers, the labeled anti-cortisol antibodies having the number from which coloring based on the labeled anti-cortisol antibodies bonded to cortisol immobilized on the substrate of the immunochromatographic test strip can be confirmed, and that the selected number of the labeled anti-cortisol antibodies are mixed with the blood sample in the step (a).

It is preferable to use the first labeled anti-cortisol antibodies or the second labeled anti-cortisol antibodies of which number is greater than that of the first labeled anti-cortisol antibodies in the step (a) from the viewpoint of determination of the amount of the cortisol contained in the blood sample in easy operation.

The number of the first labeled anti-cortisol antibodies is preferably $3 \times 10^8$ or more from the viewpoint of high-sensitive determination of the amount of the cortisol contained in the blood sample, and preferably $8 \times 10^8$ or less from the viewpoint of reduction in the cost required for the labeled anti-cortisol antibodies used in the step (a). In addition, the number of the second labeled anti-cortisol antibodies is preferably $8 \times 10^8$ or more from the viewpoint of high-sensitive determination of the amount of the cortisol contained in the blood sample, and preferably $2.4 \times 10^9$ or less from the viewpoint of reduction in the cost required for the labeled anti-cortisol antibodies used in the step (a). In this case, the selection of the labeled anti-cortisol antibodies having a number from which coloring can be confirmed can be carried out by, for instance, mixing the first number of the labeled anti-cortisol antibodies with the postcaval venous blood to conduct the antigen-antibody reaction of the cortisol contained in the postcaval venous blood with the labeled anti-cortisol antibodies, developing the resulting mixture on the immunochromatographic test strip to conduct the antigen-antibody reaction of free forms of labeled anti-cortisol antibodies in the mixture with the cortisol immobilized on the substrate of the immunochromatographic test strip, thereby bonding the antibodies to the cortisol, and then confirming the coloring based on the labeled anti-cortisol antibodies bonded to the cortisol. In this case, when the coloring could be confirmed, the first number of the labeled antibodies is used in the step (a). On the other hand, when no coloring could be confirmed, the same operation as in the case where the first labeled anti-cortisol antibodies are used is carried out by using the second number of the labeled anti-cortisol antibodies and the postcaval venous blood. Thus, the labeled anti-cortisol antibodies having a number from which coloring can be confirmed can be selected.

On the other hand, when the blood sample to be tested is used after diluting with a solvent, the number of the labeled anti-cortisol antibodies can be appropriately adjusted depending on the detection sensitivity. It is preferable that a diluted solution, which is prepared by diluting the blood sample to be tested so as to have a one-half concentration of that of the blood sample to be tested, is used in the same volume as that of the blood sample to be tested in place of the blood sample to be tested, and that $1.2 \times 10^9$ to $4.8 \times 10^9$ of the labeled anti-cortisol antibodies are used per 10 µL of the blood sample from the viewpoint of accurate determination of the amount of the cortisol in easy operation. In this case, the lower limit of the number of the labeled anti-cortisol antibodies per 10 µL of the blood sample can be a number sufficient for sensitively determining the amount of the cortisol contained in the blood sample to be tested. The upper limit of the number of the labeled anti-cortisol antibodies per 10 µL of the blood sample can be a number of the labeled anti-cortisol antibodies for reducing the cost required for the labeled anti-cortisol antibodies used and determining the amount of the cortisol contained in the blood sample in a low cost.

Next, in the step (b), the mixture obtained in the step (a) is developed on the immunochromatographic test strip having a substrate on which cortisol is immobilized to cause the antigen-antibody reaction of free forms of labeled anti-cortisol antibodies in the mixture with the cortisol immobilized on the substrate, thereby bonding cortisol to the labeled anti-cortisol antibodies.

The immunochromatographic test strip used in the step (b) has a substrate on which cortisol is immobilized. According to this immunochromatographic test strip, it is possible to develop the mixture obtained in the step (a) on the immunochromatographic test strip, thereby bonding the unreacted labeled anti-cortisol antibodies to the cortisol immobilized on the substrate.

In the immunochromatographic test strip, it is preferable that the molar amount of the cortisol immobilized on the substrate is not less than that of the labeled anti-cortisol antibodies. In this case, in the step (a), the surplus labeled anti-cortisol antibodies which are not bonded to cortisol contained in the blood sample, bond to the cortisol immobilized on the substrate. Therefore, the amount of the labeled anti-cortisol antibodies which bond to the cortisol immobilized on the substrate is the amount obtained by subtracting the amount of the labeled anti-cortisol antibodies bonded to the cortisol contained in the blood sample from the amount of the labeled anti-cortisol antibodies used in the step (a).

Thus, according to the evaluation method 1, the amount of the cortisol contained in the blood sample can be indirectly found on the basis of the amount of the labeled anti-cortisol antibodies bonded to the cortisol immobilized on the substrate of the immunochromatographic test strip. Therefore, whether or not a blood sample to be tested has a quality suitable for the adrenal vein sampling test can be easily evaluated.

Preferred immunochromatographic test strip used in the step (b) is an immunochromatographic test strip on which cortisol is immobilized via a linker from the viewpoint that the amount of cortisol contained in the blood sample to be tested is accurately determined.

The linker includes, for instance, O-carboxymethyloxime and the like. It is preferable that the linker is immobilized on the substrate via bovine serum albumin from the viewpoint that stable determination results are obtained by strongly immobilizing cortisol on the substrate.

The immunochromatographic test strip on which cortisol is immobilized via the linker can be preferably used for a kit for evaluating a blood sample. This kit for evaluating a blood sample may contain, for instance, a container required for the test and the like, beside the immunochromatographic test strip.

In the immunochromatographic test strip used in the step (b), a water-absorbing pad made of a water-absorbing material can be located downstream site of the substrate in the direction of development of the blood sample from the viewpoint of efficient development of the blood sample on the substrate. The water-absorbing material includes, for instance, nitrocellulose and the like.

The immunochromatographic test strip used in the step (b) can be easily prepared by, for instance, immobilizing cortisol on the substrate, blocking the substrate, and thereafter washing the substrate. For instance, the immunochromatographic test strip can be prepared by immobilizing cortisol on the substrate via a bovine serum albumin-conjugated linker, blocking the substrate after immobilization of cortisol, and thereafter washing the substrate.

The substrate can be a substrate made of a material on which the mixture can be developed. In addition, preferred substrate is a substrate from which a development speed sufficient for capturing the labeled anti-cortisol antibodies can be obtained by the cortisol to be immobilized on the substrate.

The development speed in the case where purified water is developed on the substrate can be appropriately controlled depending on the bonding power between the labeled anti-cortisol antibodies used and the cortisol used. The development speed in the case where the purified water is developed on the substrate is preferably 0.35 mm/sec or less, more preferably 0.32 mm/sec or less from the viewpoint of accurately quantitative determination of the labeled anti-cortisol antibodies which bond to cortisol immobilized on the substrate, and preferably 0.25 mm/sec or more, more preferably 0.28 mm/sec or more from the viewpoint of shortening the time required for the evaluation.

The substrate includes, for instance, a membrane such as a membrane made of porous polyethylene, a membrane made of a cellulose filter paper, or a membrane made of nitrocellulose. Among them, the membrane made of cellulose filter paper is preferable from the viewpoint of efficiently conducting the immobilization of cortisol and the like, the control of the development speed and the like.

The development of the mixture on the immunochromatographic test strip can be carried out by, for instance, by using as a developing solvent a liquid component contained in the mixture with the aid of capillary action.

Next, in the step (c), the amount of the labeled anti-cortisol antibodies which are bonded to cortisol in the step (b) is determined.

The amount of the labeled anti-cortisol antibodies bonded to cortisol can be determined on the basis of the amount of labeling substances in the labeled anti-cortisol antibodies. For instance, the amount of the labeling substances of the labeled anti-cortisol antibodies which are bonded to cortisol immobilized on the immunochromatographic test strip is determined. Thus, the determination of the amount of the labeled anti-cortisol antibodies can be carried out. More specifically, when the labeling substance is colloidal gold particle, the quantitative determination of the labeled anti-cortisol antibodies can be carried out by, for instance, a method for determining the absorbance of the colloidal gold particles in the labeled anti-cortisol antibodies bonded to cortisol of the immunochromatographic test strip, a method for determining the reflecting density of the colloidal gold particles and the like. The absorbance can be determined by using an absorption spectrometer. In addition, the reflecting density can be determined by using a densitometer.

From the viewpoint of easy evaluation of the quality of a blood sample, it is possible that in the step (a), the labeled anti-cortisol antibodies in an amount greater than that of antibodies reacting with cortisol contained in the peripheral blood of which volume is the same as that of the blood sample to be tested are mixed with the blood sample to be tested, thereby conducting the antigen-antibody reaction of the labeled anti-cortisol antibodies with cortisol contained in the blood sample, and that in the step (b), an immunochromatographic test strip having cortisol immobilized thereon of which amount is not less than that of cortisol reacting with the same amount of labeled anti-cortisol antibodies used in the step (a) is used. In this case, the quality of the blood sample can be easily evaluated by simply observing with the naked eyes the presence or absence of the labeling substances of the labeled anti-cortisol antibodies on the test line of the immunochromatographic test strip.

Next, in the step (d), whether or not the blood sample to be tested has a quality suitable for the adrenal vein sampling test is evaluated on the basis of the amount of the labeled anti-cortisol antibodies determined in the step (c).

In the step (d), whether or not the blood sample to be tested has a quality suitable for the adrenal vein sampling test can be evaluated by the coloring based on the labeled anti-cortisol antibodies which bond to the cortisol immobilized on the immunochromatographic test strip when the blood sample to be tested is developed on the immunochromatographic test strip in the step (b).

In addition, in the step (d), an immunochromatographic test strip in which the molar amount of cortisol immobilized on the substrate is not less than that of the labeled anti-cortisol antibodies is used to determine an intensity of the coloring caused by the labeled anti-cortisol antibodies which bond to the immobilized cortisol when the blood sample to be tested is developed on the immunochromatographic test strip. Thus, whether or not the blood sample to be tested has a quality suitable for the adrenal vein sampling test can be evaluated on the basis of the determined intensity of the coloring.

It can be judged that the blood sample has a quality suitable for the adrenal vein sampling test, in the case where the absorbance of the coloring based on the labeled anti-cortisol antibodies bonded to the cortisol immobilized on the substrate is not more than one-fourth as high as the absorbance value of the determination result of a blood sample of the postcaval vein or the case where no coloring is visually confirmed, when the immunochromatographic test strip in which the molar amount of cortisol immobilized on the substrate is not less than that of the labeled anti-cortisol antibodies is used to develop the blood sample to be tested on the immunochromatographic test strip.

In the present invention, an immunochromatographic test strip having the labeled antibody phase provided on one end of a substrate and cortisol immobilized on the other end of the substrate, wherein the labeled antibody phase holds labeled anti-cortisol antibodies so that the labeled anti-cortisol antibodies are detached by contacting with the blood sample to be tested, is used in place of the immunochromatographic test strip having a substrate on which cortisol is immobilized.

This immunochromatographic test strip having the labeled antibody phase which holds labeled anti-cortisol antibodies so that the labeled anti-cortisol antibodies are detached by contacting with the blood sample to be tested, provided on one end of a substrate and cortisol immobilized on the other end of the substrate is suitably used for a kit for evaluating a blood sample. This kit for evaluating a blood sample can include, for instance, a container necessary for the test and the like, besides the immunochromatographic test strip.

When the immunochromatographic test strip having the labeled antibody phase provided on one end of a substrate and cortisol immobilized on the other end of the substrate wherein the labeled antibody phase holds labeled anti-cortisol antibodies so that the labeled anti-cortisol antibodies are detached by contacting with the blood sample to be tested is used, the quality of a blood sample can be evaluated by the steps of:

(A) developing a blood sample to be tested in a given amount from the end of the labeled antibody phase of the immunochromatographic test strip, to cause the antigen-antibody reaction of the labeled anti-cortisol antibodies with cortisol contained in the blood sample, and thereafter subjecting free forms of labeled anti-cortisol antibodies after the antigen-antibody reaction to another antigen-antibody reaction with cortisol immobilized on the substrate, thereby bonding the antibodies to the cortisol immobilized on the substrate, (B) determining the amount of the labeled anti-cortisol antibodies bonded to the cortisol immobilized on the substrate in the step (A), and (C) evaluating whether or not the blood sample has a quality suitable for suprarenal vein sampling test on the basis of the amount of the labeled anti-cortisol antibodies determined in the step (B). Hereinafter, this method for evaluating the quality of a blood sample is referred to as "evaluation method 2".

In the step (A), the blood sample to be tested is developed in a given amount from the end of the labeled antibody phase of the immunochromatographic test strip. The development of the blood sample to be tested on the immunochromatographic test strip can be carried out by, for instance, by using as a developing solvent a liquid component contained in the blood sample with the aid of capillary action. In addition, other development solvent can be appropriately used as occasion demands. The specific examples of the development solvent include a phosphate buffer and the like.

In the evaluation method 2, the blood sample to be tested includes, for instance, plasma, serum, whole blood and the like. Among the blood samples to be tested, plasma is preferable from the viewpoint of more efficient bonding of cortisol contained in the blood sample to the labeled anti-cortisol antibodies to form a complex. On the other hand, when an immunochromatographic test strip further comprising a sample pad for dropping the blood sample to be tested to filter out hemocyte and the like, provided on the immunochromatographic test strip is used, the whole blood is preferable from the viewpoint of evaluation of the blood sample to be tested in easy operation without previously preparing a sample obtained by separating hemocyte and serum from the blood sample to be tested.

In the immunochromatographic test strip used in the step (A), the antigen-antibody reaction of the labeled anti-cortisol antibodies in an amount sufficient for visually evaluating whether or not the blood sample is collected from the suprarenal vein with cortisol contained in the blood sample can be conducted in such an easy operation that the blood sample to be tested is developed on the substrate.

The molar amount of the labeled anti-cortisol antibodies held on the labeled antibody phase of the immunochromatographic test strip is preferably larger than that of the cortisol contained in the postcaval venous blood. The upper limit of the molar amount of the labeled anti-cortisol antibodies in the labeled antibody phase can appropriately controlled taking consideration into the amount and the cost of the labeled anti-cortisol antibodies held on the substrate and the like.

In the evaluation method 2, the immunochromatographic test strip on which the labeled antibody phase is provided and cortisol is immobilized is used. Therefore, by simply developing a given amount of the blood sample to be tested on the immunochromatographic test strip, the antigen-antibody reaction of the labeled anti-cortisol antibodies with cortisol contained in the blood sample is caused to occur another antigen-antibody reaction of free forms of labeled anti-cortisol antibodies after the former antigen-antibody reaction with the cortisol immobilized on the substrate, whereby the free forms of labeled anti-cortisol antibodies after the former antigen-antibody reaction can be bonded to the cortisol immobilized on the substrate.

On the immunochromatographic test strip used in the step (A), cortisol is preferably immobilized via a linker like the immunochromatographic test strip used in the step (b) of the evaluation method 1. In addition, strong immobilization of cortisol on the substrate can be expected to give stable determination results. Therefore, it is preferable that the linker is immobilized on the substrate via bovine serum albumin.

The substrate of the immunochromatographic test strip used in the step (A) includes the same substrate as the substrate used in the immunochromatographic test strip used in the step (b).

The labeled antibody phase can be prepared by a method including the steps of applying a solution containing the labeled anti-cortisol antibodies to the substrate, and thereafter drying the substrate after application under a suitable condition, a method including the steps of applying a liquid dispersion obtained by dispersing the labeled anti-cortisol antibody in a solution containing a water-soluble compound to the substrate, and thereafter drying the substrate, and the like. Among these methods, preferred is the method including the steps of applying a liquid dispersion obtained by dispersing the labeled anti-cortisol antibodies in a solution containing a water-soluble compound to the substrate, and thereafter drying the substrate. The reason is that the labeled anti-cortisol antibodies are easily detached from the substrate when the blood sample contacts with the labeled antibody phase, and the labeled anti-cortisol antibodies are hardly detached from the substrate when the blood sample is not contacted with the labeled antibody phase.

The water-soluble compound includes, for instance, a cellulose ether, a sugar and the like. The cellulose ether includes, for instance, methyl cellulose, ethyl cellulose, carboxymethyl cellulose, carboxyethyl cellulose, oxyethyl cellulose, cyanoethyl cellulose and the like, but the present invention is not limited to those exemplified ones. In addition, the sugar includes, for instance, saccharose or the like, but the present invention is not limited to those exemplified ones.

The distance between the labeled antibody phase and the cortisol-immobilized site on the substrate can be a distance sufficient for developing a complex of the cortisol contained in the blood sample to be tested and the labeled anti-cortisol antibodies and free forms of labeled anti-cortisol antibodies which are not bonded to the cortisol contained in the blood sample to be tested on the substrate.

On the immunochromatographic test strip used in the step (A), a sample pad made of a water-absorbing material for dropping the blood sample to be tested thereto, to filter out hemocyte and the like can be located upstream site of the labeled antibody phase on the substrate in the direction of development of the blood sample from the viewpoint of evaluation of the blood sample to be tested in easy operation when the blood sample to be tested is whole blood. The water-absorbing material can be a material having a function to filter out hemocyte from whole blood. The water-absorbing material includes the same material as the water-absorbing material used in the evaluation method 1.

On the immunochromatographic test strip used in the step (A), a water-absorbing pad made of a water-absorbing material can be located downstream site of the substrate in the direction of development of the blood sample from the viewpoint of efficient development of the blood sample on the substrate. The water-absorbing material can be the same water-absorbing material as those used in the evaluation method 1.

In the step (A), the blood sample to be tested can be used as it is without dilution, when cortisol concentration in the peripheral blood of the individual is a given standard concentration. When plasma or serum is used as the blood sample to be tested, at the time of using the immunochromatographic test strip, the number of the labeled anti-cortisol antibodies held on the labeled antibody phase per 10 μL of the plasma or the serum is preferably $3 \times 10^8$ or more from the viewpoint of high-sensitive determination of the amount of cortisol contained in the plasma or serum, and preferably $9 \times 10^8$ or less from the viewpoint of reduction in the cost required for the labeled anti-cortisol antibodies. When whole blood is used as the blood sample to be tested, the number of the labeled anti-cortisol antibodies held on the labeled antibody phase per 10 μL of the whole blood is preferably $1.5 \times 10^8$ or more from the viewpoint of high-sensitive determination of the amount of cortisol contained in the whole blood, and preferably $5.4 \times 10^8$ or less from the viewpoint of reduction in the cost required for the labeled anti-cortisol antibodies. When the colloidal gold-labeled anti-cortisol antibody solution is used as a labeled anti-cortisol antibody, the amount of the colloidal gold-labeled anti-cortisol antibody solution of which absorbance at a wavelength of 520 nm is 1 to 10 abs can be adjusted to be 1 to 15 μL per 30 μL of the blood sample to be tested. The product of the absorbance multiplied by the amount of the colloidal gold-labeled anti-cortisol antibody solution can be adjusted to be 10 to 90 abs·μL.

In the step (A), when the cortisol concentration in the peripheral blood of the individual is expected to vary widely in the case where the plasma or the serum is used as a blood sample to be tested, it is preferable that two kinds of the labeled anti-cortisol antibodies are used per 10 μL of the blood sample when the blood sample to be tested is used as it is without dilution from the viewpoint of easy determination of the amount of the cortisol contained in the blood sample. In this case, the number of the labeled anti-cortisol antibodies per 10 μL of the plasma or the serum in the immunochromatographic test strip is preferably $3 \times 10^8$ or more from the viewpoint of high-sensitive determination of the amount of cortisol contained in the plasma or the serum, and preferably $2.4 \times 10^9$ or less from the viewpoint of reduction in the cost required for the labeled anti-cortisol antibodies. Here, the number of the first labeled anti-cortisol antibodies is preferably $3 \times 10^8$ or more from the viewpoint of high-sensitive determination of the amount of the cortisol contained in the plasma or the serum, and preferably $8 \times 10^8$ or less from the viewpoint of reduction in the cost required for the labeled anti-cortisol antibodies. In addition, the number of the second labeled anti-cortisol antibodies is preferably $8 \times 10^8$ or more from the viewpoint of high-sensitive determination of the amount of the cortisol contained in the plasma or the serum, and preferably $2.4 \times 10^9$ or less from the viewpoint of reduction in the cost required for the labeled anti-cortisol antibodies. It is preferable that in the step (A), the first labeled anti-cortisol antibodies or the second labeled anti-cortisol antibodies of which number is greater than that of the first labeled anti-cortisol antibodies are used as the labeled anti-cortisol antibodies held on the labeled antibody phase from the viewpoint of determining the amount of the cortisol contained in the plasma or the serum in easy operation.

In addition, from the viewpoint of determination of the amount of cortisol in a low cost in easy operation, it is more preferable to select at least two kinds of numbers of the immunochromatographic test strips each having different numbers of the labeled anti-cortisol antibodies held on the labeling antibody phase, by which the coloring based on the labeled anti-cortisol antibodies bonded to cortisol immobilized on the substrate of the immunochromatographic test strip can be confirmed by using the postcaval venous blood in place of the blood sample in the step (A), and to use the selected immunochromatographic test strips in the step (A).

In the step (A), when the cortisol concentration in the peripheral blood of the individual is expected to vary widely in the case where the whole blood is used as the blood sample to be tested, it is preferable that two kinds of the labeled anti-cortisol antibodies are used as the labeled anti-cortisol antibodies per 10 μL of the blood sample when the blood sample to be tested is used as it is without dilution from the viewpoint of easy determination of the amount of cortisol contained in the blood sample. In this case, the number of the labeled anti-cortisol antibodies in the immunochromatographic test strip per 10 μL of the whole blood is preferably $1.5 \times 10^8$ or more from the viewpoint of high-sensitive determination of the amount of cortisol contained in the whole blood, and preferably $1.44 \times 10^9$ or less from the viewpoint of reduction in the cost required for the labeled anti-cortisol antibodies. Here, the number of the first labeled anti-cortisol antibodies is preferably $1.5 \times 10^8$ or more from the viewpoint of high-sensitive determination of the amount of the cortisol contained in the whole blood, and preferably $4 \times 10^8$ or less from the viewpoint of reduction in the cost required for the labeled anti-cortisol antibodies. In addition, the number of the second labeled anti-cortisol antibodies is preferably $4 \times 10^8$ or more from the viewpoint of high-sensitive determination of the amount of the cortisol contained in the whole blood, and preferably $1.44 \times 10^9$ or less from the viewpoint of reduction in the cost required for the labeled anti-cortisol antibodies. It is preferable to use in the step (A), the first labeled anti-cortisol antibodies or the second labeled anti-cortisol antibodies of which number is greater than that of the first labeled anti-cortisol antibodies, as the labeled anti-cortisol antibodies held on the labeled antibody phase from the viewpoint of determination of the amount of the cortisol contained in the whole blood in easy operation.

When the blood sample to be tested is used as it is without dilution in the step (A), the selection of the immunochromatographic test strip can be carried out by using a immunochromatographic test strip having the first number of the labeled anti-cortisol antibodies held on the labeled antibody phase (hereinafter referred to as "test strip A") and the postcaval venous blood. The selection of the immunochromatographic test strip can be carried out by developing the postcaval venous blood from the end of the labeled antibody phase of the test strip A, and then confirming the coloring based on the labeled anti-cortisol antibodies bonded to cortisol immobilized on the substrate of the test strip A. In this case, when the coloring has been confirmed, this test strip A is used as the immunochromatographic test strip in the step (A). On the other hand, when the coloring has not been confirmed, the immunochromatographic test strip can be selected by using the immunochromatographic test strip having the second number of the labeled anti-cortisol antibodies held on the labeled antibody phase (hereinafter referred to as "test strip B") and the postcaval venous blood, to carry out the same operation as in the case where the test strip A is used.

On the other hand, when a diluted solution prepared by diluting the blood sample to be tested with a solvent is used, the number of labeled anti-cortisol antibodies can be appropriately controlled depending on the detection sensitivity. When the blood sample to be tested is plasma or serum, it is preferable that the diluted solution prepared by diluting the blood sample to be tested so as to have a one-half concentration of that of the blood sample to be tested, is used in the same volume as that of the blood sample to be tested in place of the blood sample to be tested in the step (A), and that an immunochromatographic test strip in which the number of the labeled anti-cortisol antibodies per 10 μL of the blood sample is $1.2 \times 10^9$ to $4.8 \times 10^9$ is used from the viewpoint of accurate determination of the amount of cortisol in easy operation. In this case, the lower limit of the number of the labeled anti-cortisol antibodies per 10 μL of the blood sample can be a number sufficient for sensitively determining the amount of the cortisol contained in the blood sample to be tested. The upper limit of the number of labeled anti-cortisol antibodies per 10 μL of the blood sample may be the number for lowering a cost required for the labeled anti-cortisol antibodies used to determine the amount of the cortisol contained in the blood sample to be tested in a low cost. When the blood sample to be tested is whole blood, it is preferable that the diluted solution prepared by diluting the blood sample to be tested so as to have a one-half concentration of that of the blood sample to be tested is used in the same volume as that of the blood sample to be tested in place of the blood sample to be tested in the step (A), and that an immunochromatographic test strip in which the number of the labeled anti-cortisol antibodies per 10 μL of the blood sample is $6 \times 10^8$ to $2.88 \times 10^9$ is used.

In the step (B), the amount of the labeled anti-cortisol antibodies bonded to the cortisol immobilized on the substrate in the step (A) is determined. The determination of the amount of the labeled anti-cortisol antibodies can be carried out in the same manner as in the step (c) of the evaluation method 1.

In addition, in the step (B), it is possible that the immunochromatographic test strip in which the molar amount of cortisol immobilized on the substrate is not less than that of the labeled anti-cortisol antibodies is used to determine an intensity of the coloring caused by the labeled anti-cortisol antibodies which bond to the immobilized cortisol when the blood sample to be tested is developed on the immunochromatographic test strip, and thereafter whether or not the blood sample to be tested has a quality suitable for the adrenal vein sampling test is evaluated on the basis of the determined intensity of the coloring.

There can be evaluated whether or not the blood sample to be tested has a quality suitable for the adrenal vein sampling test by using the immunochromatographic test strip in which the molar amount of cortisol immobilized on the substrate is not less than that of the labeled anti-cortisol antibodies, and coloring based on the labeled anti-cortisol antibodies which bond to the cortisol immobilized when the blood sample to be tested is developed on the immunochromatographic test strip. In this case, it is determined that the blood sample has a quality suitable for the adrenal vein sampling test, if an absorbance value is not more than one-fourth as high as the absorbance value of the determination result of the blood sample of the postcaval vein or if no coloring is visually confirmed.

In the step (C), whether or not the blood sample to be tested has a quality suitable for the adrenal vein sampling test is evaluated on the basis of the amount of the labeled anti-cortisol antibodies determined in the step (B). Evaluation of whether or not the blood sample to be tested has a quality suitable for the adrenal vein sampling test can be carried out in the same manner as in the step (d) of the evaluation method 1.

In the present invention, in place of the immunochromatographic test strip having cortisol immobilized thereon, an immunochromatographic test strip having the anti-cortisol antibodies immobilized thereon can be used.

When the immunochromatographic test strip is used, the quality of a blood sample can be evaluated by the steps of:
(I) developing the blood sample to be tested on the immunochromatographic test strip having anti-cortisol antibodies immobilized thereon, to cause the antigen-antibody reaction of cortisol contained in the blood sample with the anti-cortisol antibodies immobilized on the substrate, thereby bonding cortisol to the anti-cortisol antibodies,
(II) further developing labeled cortisol on the immunochromatographic test strip after the step (I), to cause the antigen-antibody reaction of the labeled cortisol with anti-cortisol antibodies which are not bonded to cortisol contained in the blood sample among the anti-cortisol antibodies immobilized on the substrate, thereby bonding the labeled cortisol to the anti-cortisol antibodies immobilized on the substrate,
(III) determining the amount of the labeled cortisol bonded to the anti-cortisol antibodies immobilized in the step (II),
(IV) calculating the amount of the cortisol contained in the blood sample from the amount of the labeled cortisol determined in the step (III) and the amount of the anti-cortisol antibodies immobilized on the substrate, and
(V) evaluating whether or not the blood sample has a quality suitable for suprarenal vein sampling test on the basis of the amount of the cortisol calculated in the step (IV). Hereinafter, this method for evaluating the quality of a blood sample is referred to as "evaluation method 3".

In the step (I), a blood sample to be tested is developed on the immunochromatographic test strip having anti-cortisol antibodies immobilized thereon. Thus, the antigen-antibody reaction of cortisol contained in the blood sample with the anti-cortisol antibodies immobilized on the substrate is caused to bond cortisol to the anti-cortisol antibodies. Development of the blood sample to be tested on the immunochromatographic test strip can be carried out by using as a developing solvent a liquid component contained in the blood sample with the aid of capillary action.

On one end of the substrate of the immunochromatographic test strip used in the step (I), the anti-cortisol antibodies are immobilized. This immunochromatographic test strip can be prepared by, for instance, immobilizing the anti-cortisol antibodies on the substrate, blocking the resulting substrate and thereafter washing the substrate.

The substrate can be made of a material on which the blood sample can be developed. In addition, it is preferable that the substrate is one which exhibits a development speed sufficient for capturing cortisol by the anti-cortisol antibodies immobilized on the substrate can be obtained when the blood sample is developed thereon. The development speed and the substrate can be the same as those used in the evaluation method 1.

In the step (II), the labeled cortisol is further developed on the immunochromatographic test strip after the step (I). Thus, the antigen-antibody reaction of the labeled cortisol with anti-cortisol antibodies, which are not bonded to cortisol contained in the blood sample among the anti-cortisol antibodies immobilized on the substrate, is caused to bond the labeled cortisol to the anti-cortisol antibodies immobilized on the substrate. Development of cortisol on the immunochromatographic test strip can be carried out by, for instance, using an appropriate development solvent with the aid of capillary action. The development solvent includes, for instance, a phosphate buffer and the like.

The labeled cortisol can be obtained by, for instance, bonding the labeling substance such as a colloidal metal particle or a fluorescent substance to cortisol by a conventional method.

From the viewpoint of more easy evaluation of the quality of a blood sample, it is preferable that the anti-cortisol antibodies of which amount is larger than that of antibodies reacting with cortisol contained in the same volume of a peripheral blood as that of the blood sample to be tested are immobilized, and that the amount of the labeled cortisol used in the step (II) is the same as or more than the amount of the cortisol reacting the anti-cortisol antibodies immobilized on the substrate.

In the step (III), the labeled cortisol bonded to the anti-cortisol antibodies is quantitatively determined. The quantitative determination of this labeled cortisol can be carried out on the basis of the amount of the labeling substance contained in the labeled cortisol.

In the step (IV), the amount of the cortisol contained in the blood sample is calculated from the amount of the labeled cortisol quantitatively determined in the step (III) and the amount of the anti-cortisol antibodies immobilized on the substrate.

In the step (V), whether or not the blood sample has a quality suitable for the suprarenal vein sampling test is evaluated on the basis of the amount of the cortisol calculated in the step (IV). The evaluation of whether or not the blood sample has a quality suitable for the suprarenal vein sampling test can be carried out in the same manner as in the step (e) of the evaluation method 1.

As explained above, according to the evaluation method of the present invention, the quality of a blood sample can be quickly and easily evaluated. Therefore, whether or not the blood sample is a sample suitable for the suprarenal vein sampling test can be quickly and easily evaluated.

In addition, since the labeled anti-cortisol antibodies are used in the evaluation method of the present invention, a small amount of the cortisol can be sensitively detected. Therefore, for instance, whether or not the blood sample is a sample suitable for the suprarenal vein sampling test can be easily evaluated by simply using a small amount of blood sample.

Therefore, according to the evaluation method of the present invention, a blood sample suitable for the adrenal vein sampling test can be easily obtained. Therefore, it is expected that the success ratio of the adrenal vein sampling test is increased.

According to the present invention, the source of a blood sample can be also identified. The source of a blood sample can be identified by, for instance,
(i) mixing a blood sample to be tested with labeled anti-cortisol antibodies to conduct the antigen-antibody reaction of the labeled anti-cortisol antibodies with cortisol contained in the blood sample,
(ii) developing the mixture obtained in the step (i), to cause the antigen-antibody reaction of free forms of labeled anti-cortisol antibodies in the mixture with the cortisol immobilized on the substrate, thereby bonding the labeled anti-cortisol antibodies to the cortisol,
(iii) determining the amount of the labeled anti-cortisol antibodies bonded to the cortisol in the step (ii), and
(iv) identifying the source of the blood sample on the basis of the amount of the labeled anti-cortisol antibodies determined in the step (iii).

The steps (i) to (iii) can be carried out in the same manner as the steps (a) to (c) of the evaluation method 1, respectively.

In the step (iv), the source of the blood sample is identified on the basis of the amount of the labeled anti-cortisol antibodies determined in the step (iii).

In the step (iv), the source of the blood sample can be identified by, for instance, a method for comparing the amount of the labeled anti-cortisol antibodies determined in the step (iii) (hereinafter referred to as "antibody amount a") with the amount of the labeled anti-cortisol antibodies in the case where the steps (i) to (iii) are carried out by using the same volume of the postcaval venous blood as that of the blood sample (hereinafter referred to as "antibody amount b"), and the like.

In the method, when the antibody amount a is smaller than the antibody amount b, the amount of cortisol contained in the blood sample is larger than that of cortisol contained in the postcaval venous blood. Therefore, the source of the blood sample to be tested can be identified as a vein located more close to a juxta-adrenal gland.

As mentioned above, according to the method of identifying the source of a blood sample, the source of the blood sample can be quickly and easily identified. Therefore, according to this identification method, for instance, the sampling position can be quickly and easily identified in the adrenal vein sampling test by using a catheter.

In addition, since the labeled anti-cortisol antibodies are used in this identification method, a small amount of cortisol can be sensitively detected. Therefore, for instance, accuracy of a sampling test for high invasive adrenal vein can be confirmed only by using a small amount of the blood sample.

Thus, according to the method of identifying the source of a blood sample, since the sampling position of the blood sample by using the catheter can be quickly and easily identified in high sensitivity. Therefore, it is expected that the success rate of the adrenal vein sampling test is much more increased.

In the present invention, a substance to be tested can be detected by a method including the steps of mixing a sample to be tested containing the substance to be tested with colloidal metal labeled antibodies raised against the substance to be tested while irradiating ultrasonic waves thereto, and developing the resulting mixture on an immunochromatographic test strip having a substrate on which the substance to be tested is immobilized.

According to this method, the sample to be tested containing a substance to be tested is mixed with colloidal metal labeled antibodies raised against the substance to be tested while irradiating ultrasonic waves thereto. Therefore, the method has such an advantageous merit that the substance to be tested can be sensitively detected, although in the usual case, it is sometimes difficult to detect a substance to be tested in the conventional immunochromatography by using colloidal metal-labeled antibodies. The conditions for irradiating ultrasonic waves can be the same as in the above.

EXAMPLES

Next, the present invention will be more specifically described on the basis of examples, but the present invention is not intended to be restricted by the examples.

Example 1

Preparation of Immunochromatographic Test Strip

One end (hereinafter referred to as "upstream end") of a membrane (manufactured by Millipore Corp., trade name: Hi-Flow Plus, 60 mm×4 mm) as a substrate was used as a sample supply part. A solution prepared by dissolving cortisol-3-O-carboxylmethyl-oxime-BSA (manufactured by Fitzgerald Industries Intl company) in 10 mM phosphate buffer (pH 7.5) so as to have a concentration of 1 mg/mL (hereinafter referred to as "cortisol solution") was applied to the other end so as to be arranged in linearly oriented parallel to a narrow side (hereinafter referred to as "downstream end") positioned in a longitudinal direction (a long side direction of the membrane) from the sample supply member, and thereafter the resulting membrane was dried at room temperature. Thereafter, the membrane was blocked with bovine serum albumin (manufactured by SIGMA Corporation).

An absorption pad (manufactured by Millipore Corp., 20 mm×4 mm) was pasted out downstream end positioned in a longitudinal direction from the applying part of the cortisol solution on the resulting membrane, to give an immunochromatographic test strip.

Next, whether or not cortisol-3-O-carboxylmethyl-oxime-BSA was immobilized on the membrane of the immunochromatographic test strip was examined by developing colloidal gold-labeled anti-cortisol antibodies on the membrane, and confirming whether or not a red band was visible. As a result, a red band was visible on the membrane. Therefore, it was confirmed that cortisol-3-O-carboxylmethyl-oxime-BSA was immobilized on the membrane of the immunochromatographic test strip.

From this fact, it can be seen that the immunochromatographic test strip having cortisol immobilized thereon can be obtained by bonding a linker O-carboxylmethyl-oxime and BSA (bovine serum albumin) to cortisol.

A part on which cortisol-3-O-carboxylmethyl-oxime-BSA was immobilized was used as a test line of the immunochromatographic test strip.

Comparative Example 1

A test strip was obtained in the same procedures as in Example 1 except that cortisol was used in place of cortisol-3-O-carboxylmethyl-oxime-BSA.

Next, whether or not cortisol was immobilized on the membrane of the immunochromatographic test strip was examined by developing colloidal gold-labeled anti-cortisol antibodies on the membrane, and confirming whether or not a red band was visible. As a result, no red band was visible. Therefore, it was confirmed that cortisol was not immobilized on the membrane of this test strip.

Example 2

(1) Preparation of Sample for Immunochromatography

Whole blood sample was collected from a subject by venous catheterization. FIG. 1 is a schematic explanation view of the sampling position where the blood sample is collected. In FIG. 1, 1 represents the vicinity of the inferior vena cava, 2 being the right juxta-adrenal gland, 3 being upstream site of the left adrenal gland, 4 being downstream site of the left adrenal gland, 5 being the right kidney, 6 being the left kidney, 7 being the right adrenal gland, and 8 being the left adrenal gland.

Plasma was obtained from whole blood sample in 500 µL, which was collected from the vicinity of the inferior vena cava 1 of the subject. A reaction cell was charged with 30 µL of plasma thus obtained and 2.5 µL of colloidal gold-labeled anti-cortisol antibody solution (absorbance at a wavelength of 520 nm: about 4 abs) (amount of the colloidal gold-labeled anti-cortisol antibodies). The resulting mixture thus obtained in the reaction cell was stirred lightly with a tip of a pipette.

The colloidal gold-labeled anti-cortisol antibody solution is a solution obtained by mixing anti-cortisol antibodies (manufactured by EnBioTec Laboratories Co., Ltd., trade name: anti-cortisol) with colloidal gold particles (manufactured by BBI, trade name: Gold Colloid), to give a mixture, still standing and then centrifuging the resulting mixture, removing a supernatant to remove free anti-cortisol antibodies and free colloidal gold particles therefrom, and thereafter mixing colloidal gold-labeled anti-cortisol antibodies with a buffer.

Next, the reaction cell was placed in an ultrasonic washing machine (manufactured by AS ONE Corporation) and thereafter, the mixture was stirred by generating ultrasonic waves of 42 kHz and 100 W for one minute. This mixture was used as a sample of Experimental Number 1.

In addition, a sample of Experimental Number 2, a sample of Experimental Number 3 and a sample of Experimental Number 4 were prepared in each order in the same manner as in Experimental Number 1, except that the amount of the colloidal gold-labeled anti-cortisol antibody solution was changed to 5 µL, 7.5 µL and 10 µL, respectively.

(2) Immunochromatography

The sample supply part of the immunochromatographic test strip obtained in Example 1 was soaked and allowed to stand in the mixture in the reaction cell obtained in the above (1) for 4 minutes. Thereafter, the immunochromatographic test strip was soaked in a washing liquid for 4 minutes, to wash the immunochromatographic test strip.

Next, the presence or absence of a band originated from the colloidal gold particle on the test line of this immunochromatographic test strip was observed.

Figure 2:
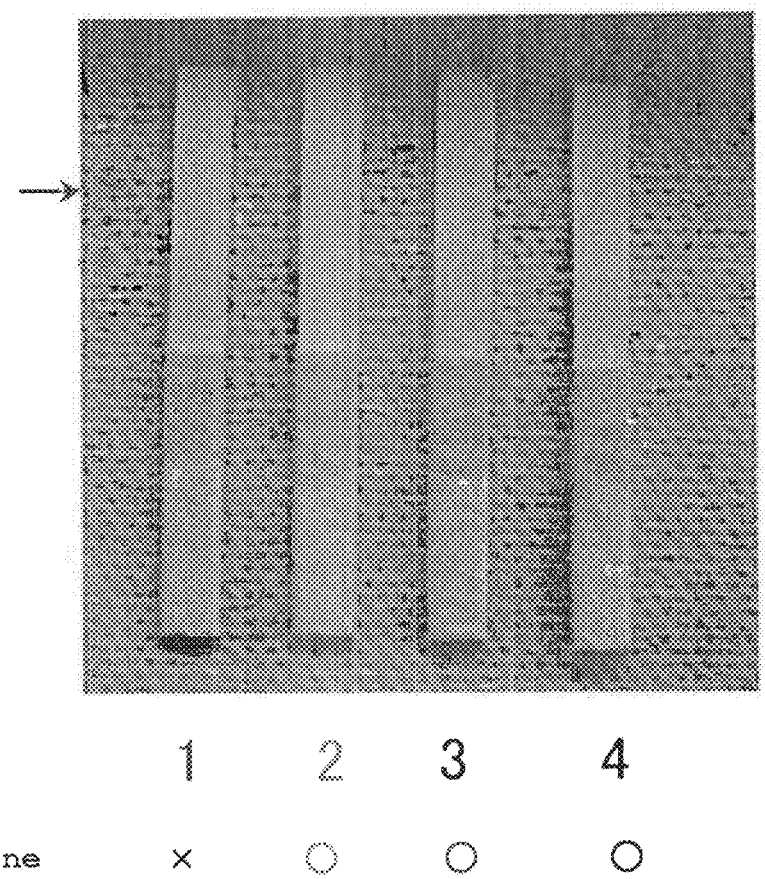
FIG. 2 is a drawing-substituting photograph of an immunochromatographic test strip showing the presence or absence of a band derived from colloidal gold particles on a test line in Example 2 according to the present invention.

The result of observing the presence or absence of a band originated from colloidal gold particles on the test line of the immunochromatographic test strip in Example 2 is shown in a drawing-substituting photograph of FIG. 2. Lane 1 is a sample of Experimental Number 1, lane 2 being a sample of Experimental Number 2, lane 3 being a sample of Experimental Number 3 and lane 4 being a sample of Experimental Number 4.

From the results shown in FIG. 2, it can be seen that a band originated from the colloidal gold particle is detected on the test line, when the amount of the colloidal gold-labeled anti-cortisol antibody solution is 5 µL or more (Experimental Number 2), that is, when the amount of the colloidal gold-labeled anti-cortisol antibody per 10 µL of a blood sample is 6.7 µL·abs ($3.8 \times 10^8$).

Therefore, it can be seen that the amount of the colloidal gold-labeled cortisol antibodies when the colloidal gold-labeled cortisol antibodies are mixed with the blood sample to conduct the antigen-antibody reaction of the colloidal gold-labeled cortisol antibodies with cortisol in the blood sample can be controlled so that the band is not visible on the test line of the immunochromatographic test strip when a blood sample to be tested is a blood sample of the vicinity of the inferior vena cava or so that the band is visible on the test line of the immunochromatographic test strip in the case where a blood sample to be tested is not a blood sample of the vicinity of the inferior vena cava.

Example 3

Immunochromatography was carried out in the same manner as in Example 2, except that each of plasma obtained from whole blood sample of postcaval vein blood collected from the vicinity of the inferior vena cava 1 of the subject in FIG. 1 (hereinafter referred to "standard sample"), plasma obtained from whole blood sample collected from the right juxta-adrenal gland 2 in FIG. 1 (hereinafter referred to "right juxta-adrenal sample"), plasma obtained from whole blood sample collected from downstream site of the left adrenal gland 3 (hereinafter referred to "sample from downstream site of the left adrenal gland") and a plasma obtained from whole blood sample collected from upstream site of the left adrenal gland 4 (hereinafter referred to "sample from upstream site of the left adrenal gland) was used as a blood sample, and that the amount of colloidal gold-labeled anti-cortisol antibody solution is adjusted to 5 µL [amounts of colloidal gold-labeled anti-cortisol antibodies: 20 µL·abs ($11.4 \times 10^8$)] or 7.5 µL [amounts of colloidal gold-labeled anti-cortisol antibodies: 30 µL·abs ($17.25 \times 10^8$)].

Next, the absorbance at a wavelength of 520 nm on the test line of each immunochromatographic test strip was determined by an absorption spectrometer [Hamamatsu Photonics K.K., trade name: Immunochromato-Reader ICA-1000].

Determination in immunochromatography for each blood samples was carried out three times. The absorbance on test line of the immunochromatographic test strip after immunochromatography when the amount of the colloidal gold-labeled anti-cortisol antibody solution is 5 µL and the amount of cortisol contained in each sample, which was calculated from the absorbance, are shown in Table 1.

TABLE 1

|  | Absorbance (abs) | Amount of cortisol (ng/mL) |
|---|---|---|
| Standard sample | 245 | 148 |
| Right juxta-adrenal sample | 16 | 347 |
| Sample from upstream site of left adrenal gland | 32 | 312 |
| Sample from downstream site of left adrenal gland | 39 | 277 |

From the results shown in Table 1, it can be seen that the absorbance of the test line in the case of the sample collected at a position near the adrenal gland, that is, the right juxta-adrenal sample, the sample from upstream site of left adrenal gland or the sample from downstream site of left adrenal gland is 16 to 39 abs, while the absorbance of the test line is 245 abs in the case of the standard sample collected from a position apart from the adrenal gland.

In addition, the absorbance on the test line of the immunochromatographic test strip after immunochromatography when the amount of the colloidal gold-labeled anti-cortisol antibody solution is 7.5 µL and the amount of the cortisol contained in each sample calculated from the absorbance are shown in Table 2.

TABLE 2

|  | Absorbance (abs) | Amount of cortisol (ng/mL) |
|---|---|---|
| Standard sample | 334 | 148 |
| Right juxta-adrenal sample | 40 | 347 |
| Sample from upstream site of left adrenal gland | 47 | 312 |
| Sample from downstream site of left adrenal gland | 51 | 277 |

From the results shown in Table 2, it can be seen that each absorbance of the right juxta-adrenal sample, the sample from upstream site of left adrenal gland and the sample from downstream site of left adrenal gland is 40 to 51 abs, while the absorbance of the standard sample is 334 abs.

In addition, from the results shown in Tables 1 and 2, the concentration of cortisol contained in the standard sample is 148 ng/mL, while the concentration of cortisol contained in the sample collected from a position near the adrenal gland is 277 to 347 ng/mL. Therefore, it can be seen that the cortisol concentration in the sample collected from the position near the adrenal is approximately twice as high as the cortisol concentration in the peripheral blood which is the standard sample.

From these results, it can be seen that the cortisol concentration contained in the blood sample has a correlation with a positional relationship such as a distance between the adrenal gland and the position in which the blood sample is collected. Therefore, it can be seen that whether or not the blood sample has a quality suitable for the adrenal vein sampling test can be judged from the amount of cortisol immobilized on the substrate and the amount of the labeled anti-cortisol antibodies bonded to the cortisol.

In addition, from the results shown in Tables 1 and 2, it can be seen that the difference in the cortisol concentration between sample from upstream site of left adrenal gland and the sample from downstream site of left adrenal gland revealed in the case where the amount of the colloidal gold-labeled anti-cortisol antibody solution is 5 µL rather than the case where the amount of the colloidal gold-labeled anti-cortisol antibody solution is 7.5 µL.

Therefore, when the difference in the positional relationship such as a distance from the adrenal is evaluated by using plasma as it is without dilution as a blood sample, it can be seen that the amount of the colloidal gold-labeled anti-cortisol antibody solution is preferably smaller.

From the above results, it can be seen that the difference in the absorbance between the samples in Tables 1 and 2 is caused by not the difference due to the operation of immunochromatography but the correlation between the concentration of cortisol contained in the blood sample and the positional relationship.

Experimental Example 1

A reaction cell was charged with 30 µL of plasma and 7.5 µL [amount of a colloidal gold-labeled anti-cortisol antibodies: 22.5 µL·abs ($13.5 \times 10^8$)] of colloidal gold-labeled anti-cortisol antibody solution [absorbance at 520 nm was about 3 abs]. Thereafter, the resulting mixture was stirred with a tip of a pipette, to give a sample of Experimental Number 5. The cortisol concentration in the plasma determined by the ELISA method was 59 ng/mL.

In addition, a sample of Experimental Number 6 was prepared in the same manner as the above, except that 10 µL [amount of colloidal gold-labeled anti-cortisol antibody: 30

μL·abs (17.7×10$^8$)] of colloidal gold-labeled anti-cortisol antibody solution was used in place of 7.5 μL of colloidal gold-labeled anti-cortisol antibody solution in Experimental Number 5.

Further, a sample of Experimental Number 7 was prepared in the same manner as the above, except that 12.5 μL [amount of colloidal gold-labeled anti-cortisol antibody: 37.5 μL·abs (22.5×10$^8$)] of colloidal gold-labeled anti-cortisol antibody solution was used in place of 7.5 μL of colloidal gold-labeled anti-cortisol antibody solution in Experimental Number 5.

Experimental Example 2

Samples of Experimental Numbers 8 to 10 were prepared in the same manner as in Experimental Example 1, except that the plasma which was different from the plasma used in Experimental Example 1 was used. Cortisol concentration in the plasma determined by the ELISA method was 403 ng/mL.

Experimental Example 3

Samples of Experimental Numbers 11 to 13 were prepared in the same manner as in Experimental Example 1, except that plasma which was different from the plasma used in each of Experimental Examples 1 and 2 was used. Cortisol concentration in the plasma determined by the ELISA method was 192 ng/mL.

Test Example 1

The sample supply part of the immunochromatographic test strip obtained by Example 1 was soaked in each sample obtained in Experimental Examples 1 to 3 contained in a reaction cell and allowed to stand for 4 minutes. Subsequently, the immunochromatographic test strip was washed by soaking the immunochromatographic test strip for 4 minutes in a washing liquid [0.1% by mass of bovine serum albumin, 0.1% by mass of Tween (registered trademark) 20, and 10 mM phosphate buffer (pH 7.5)].

Thereafter, the absorbance of the test line of each immunochromatographic test strip was determined at a wavelength of 520 nm with an absorption spectrometer [manufactured by Hamamatsu Photonics, trade name: Immunochromato-Reader ICA-1000].

The absorbance on the test line of the immunochromatographic test strip after immunochromatography is shown in Table 3.

TABLE 3

| Experimental Example | Experimental Number | Absorbance (abs) |
| --- | --- | --- |
| 1 | 5 | 207 |
|  | 6 | 318 |
|  | 7 | 296 |
| 2 | 8 | 7 |
|  | 9 | 0 |
|  | 10 | 0 |
| 3 | 11 | 30 |
|  | 12 | 36 |
|  | 13 | 33 |

From the results shown in Table 3, it can be seen that in the case of the plasma having a cortisol concentration of 59 ng/mL (Experimental Example Number 1), the absorbance on the test line of the immunochromatographic test strip is maximum when the sample of Experimental Number 6 (amount of the colloidal gold-labeled anti-cortisol antibody solution: 10 μL) is used.

In addition, it can be seen that the absorbance on the test line of the immunochromatographic test strip is larger in the case where the amount of the colloidal gold-labeled anti-cortisol antibody solution is 10 μL than the case where the amount of the colloidal gold-labeled anti-cortisol antibody solution is 7.5 μL.

The absorbance on the test line of the immunochromatographic test strip is not increased even when the amount of the colloidal gold-labeled anti-cortisol antibody solution is 10 μL or more. Therefore, it is considered that the cortisol immobilized on the substrate of the immunochromatographic test strip is almost saturated with colloidal gold-labeled anti-cortisol antibodies.

When the colloidal gold-labeled anti-cortisol antibodies were bonded to all cortisol immobilized on the substrate of the immunochromatographic test strip, the absorbance on the test line of the immunochromatographic test strip becomes about 300 abs. Therefore, it is considered that almost all cortisol immobilized on the immunochromatographic test strip are bonded to the colloidal gold-labeled anti-cortisol antibodies, and free forms of colloidal gold-labeled anti-cortisol antibodies are present in the sample of Experimental Number 6 and the sample of Experimental Number 7 (amount of the colloidal gold-labeled anti-cortisol antibody solution: 12.5 μL) in Experimental Example 1.

Test Example 2

(1) Preparation of Sample for Immunochromatography

A reaction cell was charged with 30 μL of plasma having a cortisol concentration of 59 ng/mL and 5 μL [amount of the colloidal gold-labeled anti-cortisol antibodies: 20 μL·abs (11.5×10$^8$)] of the colloidal gold-labeled anti-cortisol antibody solution (absorbance at 520 nm: about 4 abs). Thereafter, the mixture obtained in a reaction cell was stirred lightly with a tip of a pipette. The resulting mixture was used as a sample of Experimental Number 14.

In addition, a sample was prepared in the same manner as the above, except that the plasma having a cortisol concentration of 192 ng/mL is used in place of plasma having a cortisol concentration of 59 ng/mL in Experimental Number 14. The resulting sample was used as a sample of Experimental Number 15.

A reaction cell charged with the sample of Experimental Number 14 was set in an ultrasonic washing machine (manufactured by AS ONE Corporation). Thereafter, the sample was stirred by generating ultrasonic waves of 42 kHz and 100 W for 1 minute. The sample after stirring was used as a sample of Experimental Number 16.

In addition, a sample was prepared in the same manner as the above, except that the plasma having a cortisol concentration of 192 ng/mL was used in place of the plasma having a cortisol concentration of 59 ng/mL in Experimental number 16, and was used as a sample of Experimental Number 17.

(2) Immunochromatography

The sample supply part of the immunochromatographic test strip obtained in Example 1 was soaked in the sample obtained in the above (1) contained in a reaction cell, and then allowed to stand for 4 minutes. Thereafter, the presence or absence of the band originated from the colloidal gold particle on the test line of each immunochromatographic test strip was observed. The immunochromatographic test strip is shown in FIG. 3 which is a drawing-substituting photograph of the immunochromatographic test strip.

Figure 3:
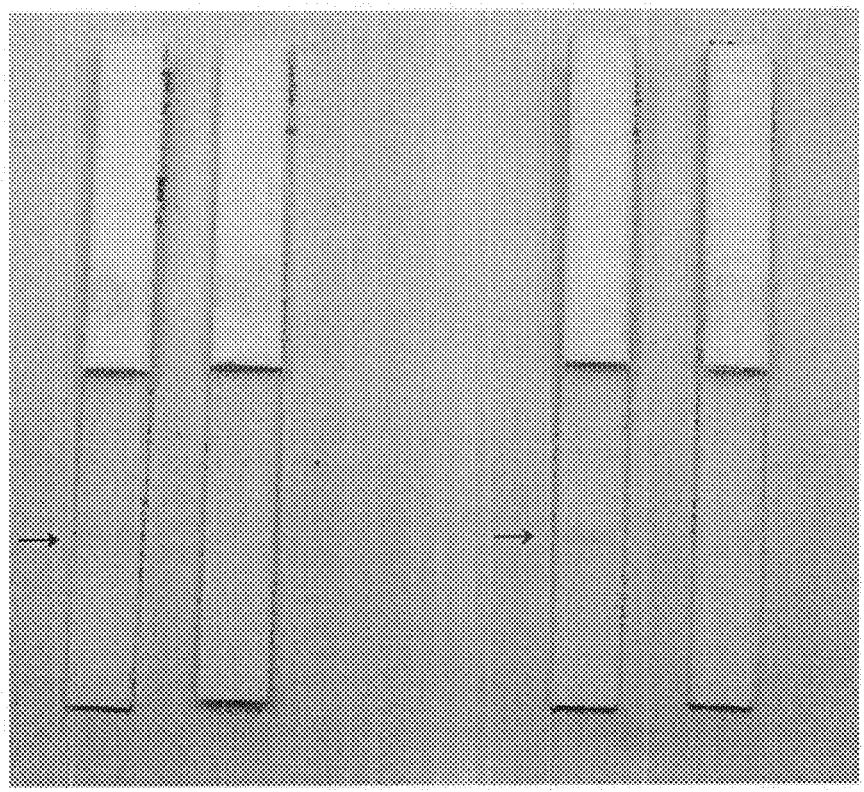
FIG. 3 is a drawing-substituting photograph of an immunochromatographic test strip showing the presence or absence of a band derived from colloidal gold particles on a test line in Test Example 2.

In FIG. 3, 1 represents the immunochromatographic test strip to which the sample of Experimental Number 14 was applied, 2 being the immunochromatographic test strip to which the sample of Experimental Number 15 was applied, 3 being the immunochromatographic test strip to which the sample of Experimental Number 16 was applied, and 4 being the immunochromatographic test strip to which the sample of Experimental Number 17 was applied.

In addition, the absorbance on the test line of each immunochromatographic test strip was determined at a wavelength of 520 nm with an absorption spectrometer [Hamamatsu Photonics K.K., trade name: Immunochromato-Reader ICA-1000].

From the results shown in FIG. 3, since the mixture of plasma and colloidal gold-labeled anti-cortisol antibody was irradiated with ultrasonic waves, it can be seen that the coloring of the band on the test line of the immunochromatographic test strip to which the sample of Experimental Number 16 was applied is stronger than that of the band on the test line of the immunochromatographic test strip to which the sample of Experimental Number 14 was applied.

The absorbance at a wavelength of 520 nm on the test line of the immunochromatographic test strip to which the sample of Experimental Number 14 was applied was 167 abs. The absorbance at a wavelength of 520 nm on the test line of the immunochromatographic test strip to which the sample of Experimental Number 16 was applied was 288 abs.

On the other hand, it can be seen that the band is not found on the test line of the immunochromatographic test strip to which the sample of Experimental Number 15 and Experimental Number 17 each of which cortisol concentration is higher than that of Experimental Number 14 or Experimental Number 16.

When the antigen-antibody reaction was inhibited by irradiating ultrasonic waves to the sample, it is considered that the band would be visible on the test line of the immunochromatographic test strip in the case where the sample having a high cortisol concentration was used. However, while the band is not visible on the test line in any one of Experimental Numbers 15 in which the sample has not been irradiated with ultrasonic waves and Experimental Numbers 17 in which the sample has been irradiated with ultrasonic wave, the band is visible on the test line in each of Experimental Numbers 14 and Experimental Numbers 16 each having a low cortisol concentration. From this, it can be seen that free forms of colloidal gold-labeled anti-cortisol antibodies can be detected with higher accuracy by irradiating ultrasonic waves to the mixture of the plasma and the colloidal gold-labeled anti-cortisol antibody solution.

Experimental Example 4

An immunochromatographic test strip of Experimental Number 18 was prepared in the same manner as in Example 1 except that a membrane having a development speed of 0.45 mm/sec when purified water was developed (manufactured by Millipore Corporation, the trade name: Hi-Flow Plus, 60 mm×4 mm) was used as a membrane.

Experimental Example 5

An immunochromatographic test strip of Experimental Number 19 was prepared in the same manner as in Experimental Example 4 except that a membrane having a development speed of 0.30 mm/sec when purified water was developed (manufactured by Millipore Corporation, the trade name: Hi-Flow Plus, 60 mm×4 mm) was used as a membrane in place of the membrane having a development speed of 0.45 mm/sec when purified water was developed.

Experimental Example 6

An immunochromatographic test strip of Experimental Number 20 was prepared in the same manner as in Experimental Example 4 except that a membrane having a development speed of 0.22 mm/sec when purified water was developed (manufactured by Millipore Corporation, the trade name: Hi-Flow Plus, 60 mm×4 mm) was used as a membrane in place of the membrane having a development speed of 0.45 mm/sec when purified water was developed.

Test Example 3

A reaction cell was charged with 30 μL of plasma having a cortisol concentration of 59 ng/mL and 5 μL [amount of the colloidal gold-labeled anti-cortisol antibodies: 25 μL·abs $(15\times10^8)$] of the colloidal gold-labeled anti-cortisol antibody solution (absorbance at 520 nm: about 5 abs). Thereafter, the mixture obtained in the reaction cell was stirred lightly with a tip of a pipette.

Next, the reaction cell was set in an ultrasonic washing machine (manufactured by AS ONE Corporation). Thereafter, ultrasonic waves of 42 kHz and 100 W was generated for 1 minute, thereby stirring the mixture to give a sample.

The sample supply part of the immunochromatographic test strip of Experimental Number 18 was soaked in the sample in the reaction cell, and then allowed to stand for 4 minutes. Thereafter, the membrane of the test strip was washed by soaking the immunochromatographic test strip in a washing liquid [0.1% by mass of bovine serum albumin, 0.1% by mass of Tween (registered trademark) 20, and 10 mM phosphate buffer (pH 7.5)] for 4 minutes.

Subsequently, the band originated from colloidal gold particles on the membrane was observed. In addition, the absorbance of the band generated on the membrane was determined at a wavelength of 520 nm with an absorption spectrometer [Hamamatsu Photonics K.K., the trade name: Immunochromato-Reader ICA-1000].

The band originated from the colloidal gold particles on the membrane was observed and then the absorbance at a wavelength of 520 nm of the band generated on the membrane was determined in the same manner as the above except that the immunochromatographic test strip of Experimental Number 19 was used in place of the immunochromatographic test strip of Experimental Number 18.

In addition, the band originated from the colloidal gold particles on the membrane was observed and then the absorbance at a wavelength of 520 nm of the band generated on the membrane was determined in the same manner as the above except that the immunochromatographic test strip of Experimental Number 20 was used in place of the immunochromatographic test strip of Experimental Number 18.

Figure 4:
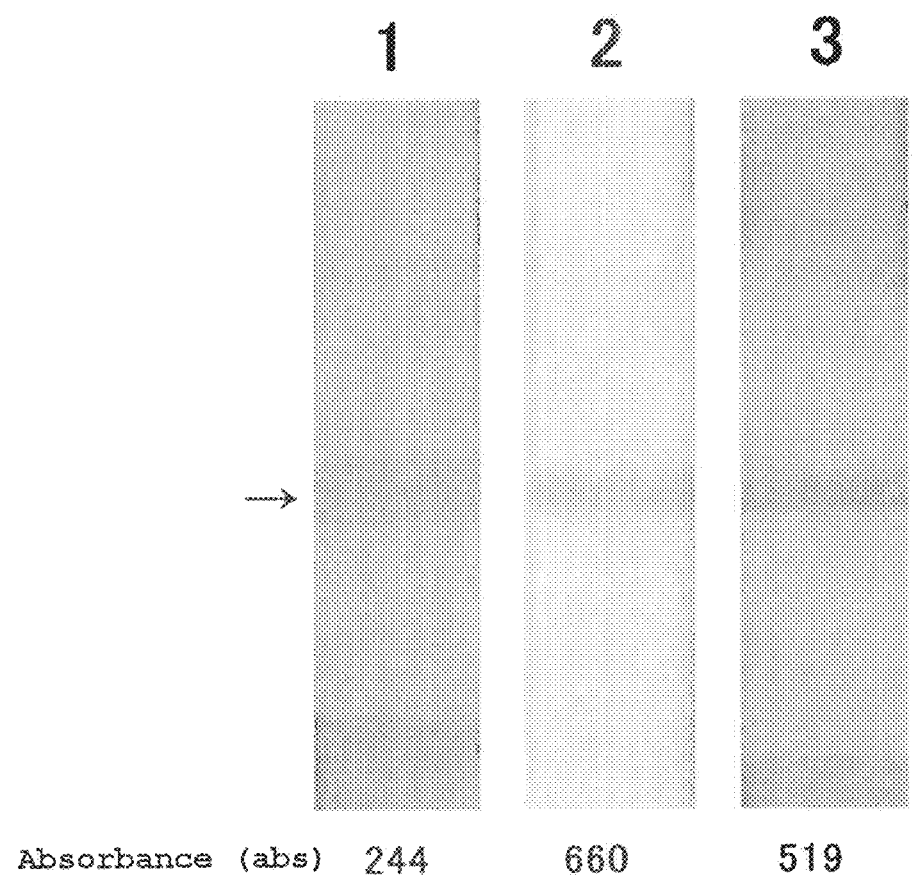
FIG. 4 is a drawing-substituting photograph of an immunochromatographic test strip after immunochromatography in Test Example 3.

The membrane after immunochromatography in Test Example 3 is shown in FIG. 4 which is a drawing-substituting photograph. In FIG. 4, 1 represents the membrane of Experimental Number 18, 2 being the membrane of Experimental Number 19, and 3 being the membrane of Experimental Number 20. In addition, the absorbance in each band was shown in the bottom of each membrane.

From the results shown in FIG. 4, it can be seen that the absorbance of the band originated from the colloidal gold particles on the membrane of Experimental Number 19 is 660 abs, which is the highest absorbance. In addition, regarding the width of the band originated from the colloidal gold particles on the membrane, it can be seen that Experimental Number 18 shows the broadest width, and Experimental Number 20 shows the narrowest width. From this, it can be seen that the band originated from the colloidal gold particles on the membrane can be easily detected by using a membrane having a development speed of 0.22 mm/sec or more and 0.45 mm/sec or less, and in particular, a membrane having a development speed of 0.30 mm/sec.

From the above-mentioned results, according to the method for evaluating the quality of a blood sample of the present invention, it can be seen that the quality of a blood sample can be quickly and easily evaluated by using a small amount of a blood sample.

Experimental Example 7

A reaction cell was charged with 10 µL of plasma having a cortisol concentration of 57 ng/mL (Experimental Number 21), 170 ng/mL (Experimental Number 22), 231 ng/mL (Experimental Number 23), 318 ng/mL (Experimental Number 24), 384 ng/mL (Experimental Number 25), 517 ng/mL (Experimental Number 26), 586 ng/mL (Experimental Number 27) or 770 ng/mL (Experimental Number 28) and 20 µL [amount of the colloidal gold-labeled cortisol antibodies: 100 µL·abs ($6 \times 10^9$)] of the colloidal gold-labeled cortisol antibody solution [absorbance at a wavelength of 520 nm was about 5 abs]. Thereafter, the resulting mixture was stirred lightly with a top of a pipette in the reaction cell, to give samples of Experimental Numbers 21 to 28.

Experimental Example 8

A reaction cell was charged with 10 µL of plasma having a cortisol concentration of 57 ng/mL (Experimental Number 29), 231 ng/mL (Experimental Number 30), 318 ng/mL (Experimental Number 31), 384 ng/mL (Experimental Number 32), 517 ng/mL (Experimental Number 33) or 586 ng/mL (Experimental Number 34) and 6 µL [amount of the colloidal gold-labeled anti-cortisol antibodies: 30 µL·abs ($1.8 \times 10^9$)] of the colloidal gold-labeled anti-cortisol antibody solution [absorbance at a wavelength of 520 nm was about 5 abs]. Thereafter, the resulting mixture was lightly stirred with a tip of a pipette in the reaction cell.

Experimental Example 9

A reaction cell was charged with 10 µL of plasma having a cortisol concentration of 57 ng/mL (Experimental Number 35), 77 ng/mL (Experimental Number 36), 110 ng/mL (Experimental Number 37), 137 ng/mL (Experimental Number 38), 170 ng/mL (Experimental Number 39), 202 ng/mL (Experimental Number 40), 218 ng/mL (Experimental Number 41), 231 ng/mL (Experimental Number 42), 242 ng/mL (Experimental Number 43), 318 ng/mL (Experimental Number 44), 384 ng/mL (Experimental Number 45) or 517 ng/mL (Experimental Number 46) and 2 µL [amount of the colloidal gold-labeled anti-cortisol antibodies: 10 µL·abs ($6 \times 10^8$)] of the colloidal gold-labeled anti-cortisol antibody solution [absorbance at a wavelength of 520 nm was about 5 abs]. Thereafter, the resulting mixture was stirred with a tip of a pipette in the reaction cell, to give samples of Experimental Numbers 35 to 46.

Experimental Example 10

Plasma having a cortisol concentration of 57 ng/mL (Experimental Number 47), 77 ng/mL (Experimental Number 48), 110 ng/mL (Experimental Number 49), 137 ng/mL (Experimental Number 50), 170 ng/mL (Experimental Number 51), 202 ng/mL (Experimental Number 52), 218 ng/mL (Experimental Number 53), 231 ng/mL (Experimental Number 54), 242 ng/mL (Experimental Number 55), 318 ng/mL (Experimental Number 56), 384 ng/mL (Experimental Number 57), 517 ng/mL (Experimental Number 58), 586 ng/mL (Experimental Number 59), 770 ng/mL (Experimental Number 60), 862 ng/mL (Experimental Number 61) or 1630 ng/mL (Experimental Number 62) was diluted with a diluent solution [composition: 0.1% by mass of bovine serum albumin and 10 mM phosphate buffer (pH 7.5)] so as to have a one-half cortisol concentration of that of the plasma. A reaction cell was charged with 10 µL of the resulting diluted solution and 10 µL [amount of the colloidal gold-labeled anti-cortisol antibodies: 50 µL·abs ($3 \times 10^9$)] of the colloidal gold-labeled anti-cortisol antibody solution [absorbance at a wavelength of 520 nm was about 5 abs]. Thereafter, the resulting mixture was stirred with a tip of a pipette in the reaction cell, to give samples of Experimental Numbers 47 to 62.

Experimental Example 11

Samples of Experimental Numbers 63 to 78 were obtained in the same manner as in Experimental Example 10 except that plasma having a cortisol concentration of 57 ng/mL (Experimental Number 63), 77 ng/mL (Experimental Number 64), 110 ng/mL (Experimental Number 65), 137 ng/mL (Experimental Number 66), 170 ng/mL (Experimental Number 67), 202 ng/mL (Experimental Number 68), 218 ng/mL (Experimental Number 69), 231 ng/mL (Experimental Number 70), 242 ng/mL (Experimental Number 71), 318 ng/mL (Experimental Number 72), 384 ng/mL (Experimental Number 73), 517 ng/mL (Experimental Number 74), 586 ng/mL (Experimental Number 75), 770 ng/mL (Experimental Number 76), 862 ng/mL (Experimental Number 77) or 1630 ng/mL (Experimental Number 78) was diluted so as to have a one-fifth cortisol concentration of that of the plasma in place of diluting plasma so as to have a one-half cortisol concentration of that of the plasma in Experimental Example 10.

Test Example 4

The sample supply part of the immunochromatographic test strip of Example 1 was soaked in any one of samples of Experimental Numbers 21 to 78 obtained by Experimental Examples 7 to 11 in the reaction cell, and then allowed to stand for 4 minutes. Thereafter, the membrane of the immunochromatographic test strip was washed by soaking the membrane for 4 minutes in a washing liquid [0.1% by mass of bovine serum albumin, 0.1% by mass of Tween (registered trademark) 20, and 10 mM phosphate buffer (pH 7.5)].

The band originated from colloidal gold particles on the washed membrane was observed and an absorbance of the band generated on the membrane was determined at a wavelength of 520 nm with an absorption spectrometer [Hamamatsu Photonics K.K., trade name: Immunochromato-Reader ICA-1000]. Relationship between the cortisol concentration and the absorbance is shown in FIG. 5.

Figure 5:
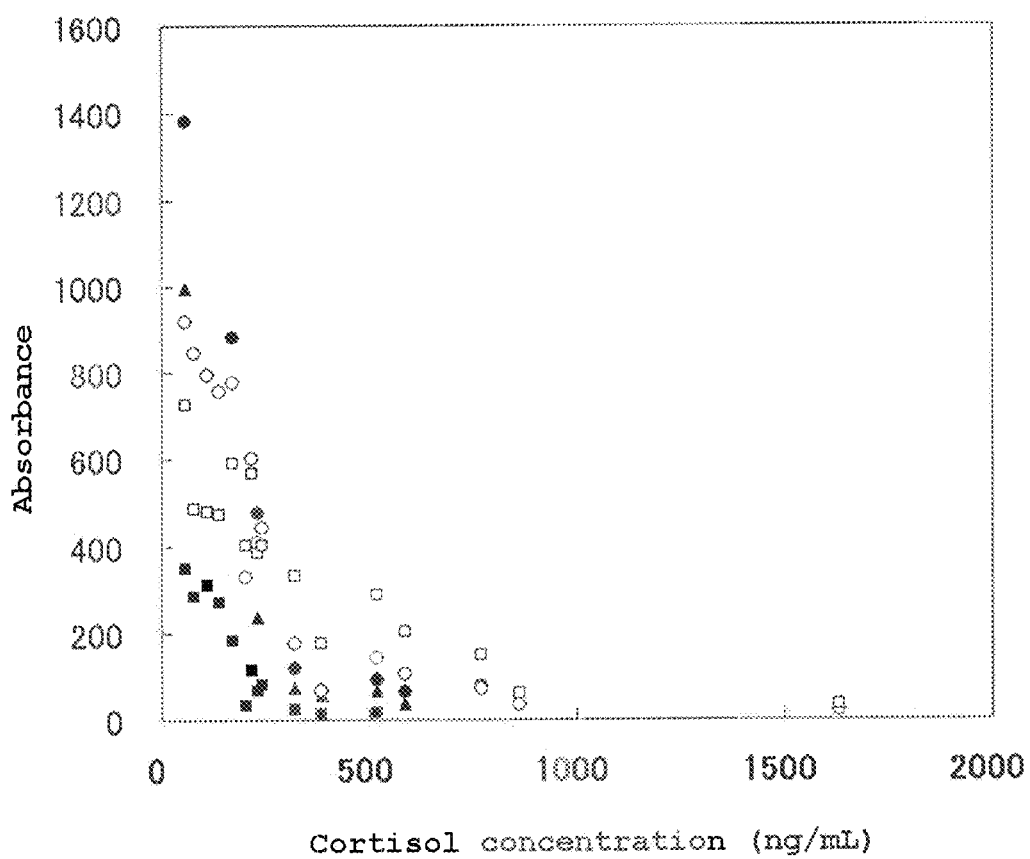
FIG. 5 is a graph showing the relationship between cortisol concentration and an absorbance in Test Example 4.

In FIG. 5, a closed circle represents the absorbance in the case where the mixture of 10 µL of plasma and 20 µL of the colloidal gold-labeled anti-cortisol antibody solution was used in Experimental Example 7, a closed triangle being the absorbance in the case where the mixture of 10 µL of plasma and 6 µL of the colloidal gold-labeled anti-cortisol antibody solution was used in Experimental Example 8, a closed square being the absorbance in the case where the mixture of 10 μL of plasma and 2 μL of the colloidal gold-labeled anti-cortisol antibody solution was used in Experimental Example 9, an open circle being the absorbance in the case where the mixture of 10 μL of the diluted solution prepared by diluting plasma so as to have a one-half concentration of that of the plasma and 6 μL of the colloidal gold-labeled anti-cortisol antibody solution was used in Experimental Example 10, and an open square being the absorbance in the case where the mixture of 10 μL of the diluted solution prepared by diluting plasma so as to have a one-fifth concentration of that of the plasma and 6 μL of the colloidal gold-labeled anti-cortisol antibody solution was used in Experimental Example 11.

From the results shown in FIG. 5, in the case where plasma was used as it is without dilution (the closed circle, the closed triangle and the closed square in FIG. 5), it can be seen that the degree of the change in the absorbance due to the difference in the cortisol concentration is large in plasma having a low cortisol concentration (cortisol concentration: 0 to 200 ng/mL). Therefore, it can be seen that the difference in the cortisol concentration is easily differentiated. On the other hand, the change in the absorbance due to the difference in the cortisol concentration is small in plasma having a high cortisol concentration (cortisol concentration: 200 to 900 ng/mL). Therefore, it can be seen that the difference in the cortisol concentration is not easily differentiated.

In the case where a diluted solution prepared by diluting plasma so as to have a one-fifth concentration of that of the plasma was used (the open square in FIG. 5), the change in the absorbance due to the difference in the cortisol concentration is large in the plasma having a high cortisol concentration (cortisol concentration: 200 to 900 ng/mL). Therefore, it can be seen that the difference in the cortisol concentration is easily differentiated. On the other hand, in the case where the cortisol concentration is low (cortisol concentration: 0 to 200 ng/mL), the change in the absorbance due to the difference in the cortisol concentration is small. Therefore, it can be seen that the difference in the cortisol concentration is not easily differentiated.

Alternatively, in the case where a diluted solution prepared by diluting plasma so as to have a one-half concentration of that of the plasma was used (the open circle in FIG. 5), the change in the absorbance due to the difference in the cortisol concentration is large in any one of the plasma having a low cortisol concentration (cortisol concentration: 0 to 200 ng/mL) and the plasma having a high concentration (cortisol concentration: 200 to 900 ng/mL). Therefore, it can be seen that the difference in the cortisol concentration is easily differentiated. From these, the change in the absorbance due to the difference in the cortisol concentration is large when plasma as a blood sample was diluted so as to have a one-fifth to one-half concentration of that of the plasma. Therefore, it can be seen that the difference in the cortisol concentration become to be easily differentiated.

Experimental Example 12

Using a diluent solution [composition: 0.1% by mass of bovine serum albumin and 10 mM phosphate buffer (pH 7.5)], plasma having a cortisol concentration of 57 ng/mL was diluted so as to have a one-half cortisol concentration of that of the plasma. A reaction cell was charged with 10 μL of the resulting diluted solution and 3 μL (Experimental Number 79), 6 μL (Experimental Number 80), 10 μL (Experimental Number 81), 15 μL (Experimental Number 82), 20 μL (Experimental Number 83) or 30 μL (Experimental Number 84) of colloidal gold-labeled anti-cortisol antibody solution (absorbance at 520 nm is about 5 abs, and the concentration of the colloidal gold-labeled anti-cortisol antibodies: $3 \times 10^8$ μL). Thereafter, each mixture obtained was stirred with a tip of a pipette, to give samples of Experimental Numbers 79 to 84.

Experimental Example 13

Samples of Experimental Number 85 (amount of colloidal gold-labeled anti-cortisol antibody solution: 3 μL), Experimental Number 86 (amount of colloidal gold-labeled anti-cortisol antibody solution: 6 μL), Experimental Number 87 (amount of colloidal gold-labeled anti-cortisol antibody solution: 10 μL), Experimental Number 88 (amount of colloidal gold-labeled anti-cortisol antibody solution: 15 μL), Experimental Number 89 (amount of colloidal gold-labeled anti-cortisol antibody solution: 20 μL) and Experimental Number 90 (amount of colloidal gold-labeled anti-cortisol antibody solution: 30 μL) were obtained in the same manner as in Experimental Example 12, except that plasma having a cortisol concentration of 90 ng/mL was used in place of the plasma having a cortisol concentration of 57 ng/mL in Experimental Example 12.

Experimental Example 14

Samples of Experimental Number 91 (amount of colloidal gold-labeled anti-cortisol antibody solution: 3 μL), Experimental Number 92 (amount of colloidal gold-labeled anti-cortisol antibody solution: 6 μL), Experimental Number 93 (amount of colloidal gold-labeled anti-cortisol antibody solution: 10 μL), Experimental Number 94 (amount of colloidal gold-labeled anti-cortisol antibody solution: 15 μL), Experimental Number 95 (amount of colloidal gold-labeled anti-cortisol antibody solution: 20 μL) and Experimental Number 96 (amount of colloidal gold-labeled anti-cortisol antibody solution: 30 μL) were obtained in the same manner as in Experimental Example 12, except that plasma having a cortisol concentration of 128 ng/mL was used in place of the plasma having a cortisol concentration of 57 ng/mL in Experimental Example 12.

Test Example 5

The sample supply part of the immunochromatographic test strip of Example 1 was soaked in any one of samples of Experimental Numbers 79 to 96 in the reaction cell, and then allowed to stand for 4 minutes. Thereafter, the membrane of the immunochromatographic test strip was soaked in a washing liquid [0.1% by mass of bovine serum albumin, 0.1% by mass of Tween (registered trademark) 20, and 10 mM phosphate buffer (pH 7.5)] for 4 minutes, to wash the membrane.

Next, the band originated from colloidal gold particles on the membrane was observed, and the absorbance of the band generated in the membrane was determined at a wavelength of 520 nm with an absorption spectrometer [Hamamatsu Photonics K.K., trade name: Immunochromato-Reader ICA-1000].

The difference in the absorbance between bands which are caused by two samples each having different cortisol concentrations was calculated on the basis of the determined absorbance, in the case where the colloidal gold-labeled anti-cortisol antibody solution was used in the same volume (same amount of colloidal gold-labeled anti-cortisol antibodies). More specifically, the difference between the absorbance of the band caused by the sample having a cortisol concentration of 57 ng/mL (Experimental Numbers 79 to 84) and the absorbance of the band caused by the sample having a cortisol concentration of 90 ng/mL (Experimental Numbers 85 to 90)

when the same volume of the colloidal gold-labeled anti-cortisol antibody solution (same amount of colloidal gold-labeled anti-cortisol antibodies) was used therefor was calculated.

The difference between the absorbance of the band caused by the sample having a cortisol concentration of 57 ng/mL (Experimental Numbers 79 to 84) and the absorbance of the band caused by the sample having a cortisol concentration of 128 ng/mL (Experimental Numbers 91 to 96) when the colloidal gold-labeled anti-cortisol antibody solution was used in the same volume (same amount of colloidal gold-labeled anti-cortisol antibody) was calculated in the same manner as the above.

Figure 6:
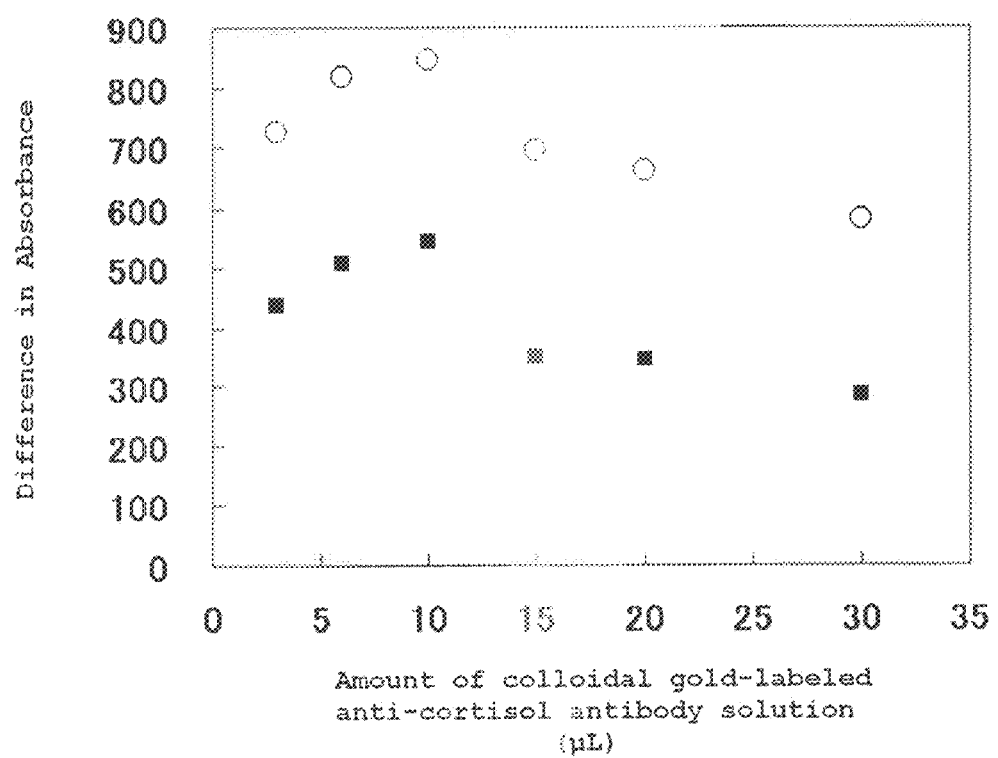
FIG. 6 is a graph showing the relationship between the amount of colloidal gold-labeled anti-cortisol antibody solution and the difference in the absorbance in Test Example 5.

The relationship between the amount of colloidal gold-labeled anti-cortisol antibody solution and the difference in the absorbance is shown in FIG. 6. In FIG. 6, a closed square represents the difference in the absorbance between the sample having a cortisol concentration of 57 ng/mL and the sample having a cortisol concentration of 90 ng/mL, and an open circle being the difference in the absorbance between the sample having a cortisol concentration of 57 ng/mL and the sample having a cortisol concentration of 128 ng/mL.

From the results shown in FIG. 6, it can be seen that the difference in the absorbance in the case where the amount of the colloidal gold-labeled anti-cortisol antibody solution is about 5 to 13 µL is larger than the difference in the absorbance in the case where the amount of the colloidal gold-labeled anti-cortisol antibody solution exceeds 15 µL. Therefore, it can be seen that the difference in the cortisol concentration become to be easily differentiated, by adjusting the amount of the colloidal gold-labeled anti-cortisol antibody solution to 5 to 13 µL when the sample having a low cortisol concentration (cortisol concentration: 0 to 200 ng/mL) is evaluated.

Experimental Example 15

Using a diluent solution [composition: 0.1% by mass of bovine serum albumin and 10 mM phosphate buffer (pH 7.5)], plasma having a cortisol concentration of 242 ng/mL was diluted so as to have a one-half cortisol concentration of that of the plasma. A reaction cell was charged with 10 µL of the resulting diluted solution and 2 µL (Experimental Number 97), 3 µL (Experimental Number 98), 4 µL (Experimental Number 99), 6 µL (Experimental Number 100), 8 µL (Experimental Number 101), 10 µL (Experimental Number 102), 15 µL (Experimental Number 103), 20 µL (Experimental Number 104) or 30 µL (Experimental Number 105) of colloidal gold-labeled anti-cortisol antibody solution (absorbance at 520 nm is about 5 abs, a concentration of the colloidal gold-labeled anti-cortisol antibodies: $3 \times 10^8$ µL). Thereafter, each mixture obtained was stirred with a tip of a pipette, to give samples of Experimental Numbers 97 to 105.

Experimental Example 16

Samples of Experimental Number 106 (amount of colloidal gold-labeled anti-cortisol antibody solution: 2 µL), Experimental Number 107 (amount of colloidal gold-labeled anti-cortisol antibody solution: 3 µL), Experimental Number 108 (amount of colloidal gold-labeled anti-cortisol antibody solution: 4 µL), Experimental Number 109 (amount of colloidal gold-labeled anti-cortisol antibody solution: 6 µL), Experimental Number 110 (amount of colloidal gold-labeled anti-cortisol antibody solution: 8 µL), Experimental Number 111 (amount of colloidal gold-labeled anti-cortisol antibody solution: 10 µL), Experimental Number 112 (amount of colloidal gold-labeled anti-cortisol antibody solution: 15 µL), Experimental Number 113 (amount of colloidal gold-labeled anti-cortisol antibody solution: 20 µL) and Experimental Number 114 (amount of colloidal gold-labeled anti-cortisol antibody solution: 30 µL) were obtained in the same manner as in Experimental Example 12, except that plasma having a cortisol concentration of 808 ng/mL was used in place of the plasma having a cortisol concentration of 242 ng/mL in Experimental Example 15.

Experimental Example 17

Samples of Experimental Number 115 (amount of colloidal gold-labeled anti-cortisol antibody solution: 2 µL), Experimental Number 116 (amount of colloidal gold-labeled anti-cortisol antibody solution: 3 µL), Experimental Number 117 (amount of colloidal gold-labeled anti-cortisol antibody solution: 4 µL), Experimental Number 118 (amount of colloidal gold-labeled anti-cortisol antibody solution: 6 µL), Experimental Number 119 (amount of colloidal gold-labeled anti-cortisol antibody solution: 8 µL), Experimental Number 120 (amount of colloidal gold-labeled anti-cortisol antibody solution: 10 µL), Experimental Number 121 (amount of colloidal gold-labeled anti-cortisol antibody solution: 15 µL), Experimental Number 122 (amount of colloidal gold-labeled anti-cortisol antibody solution: 20 µL) and Experimental Number 123 (amount of colloidal gold-labeled anti-cortisol antibody solution: 30 µL) were obtained in the same manner as in Experimental Example 12, except that plasma having a cortisol concentration of 2380 ng/mL was used in place of the plasma having a cortisol concentration of 242 ng/mL in Experimental Example 15.

Test Example 6

The sample supply part of the immunochromatographic test strip of Example 1 was soaked in any one of samples of Experimental numbers 97 to 123 each obtained by Experimental Examples 15 to 17 in the reaction cell, and then allowed to stand for 4 minutes. Thereafter, the membrane of immunochromatographic test strip was soaked in a washing liquid [0.1% by mass of bovine serum albumin, 0.1% by mass of Tween (registered trademark) 20, and 10 mM phosphate buffer (pH 7.5)] for 4 minutes, to wash the membrane.

Next, the band originated from colloidal gold particles on the membrane was observed and the absorbance of the band generated on the membrane was determined at a wavelength of 520 nm with an absorption spectrometer [Hamamatsu Photonics K.K., trade name: Immunochromato-Reader ICA-1000].

Next, the difference in the absorbance between bands caused by two samples each having different cortisol concentrations was calculated on the basis of the determined absorbance, in the case where the same volume of the colloidal gold-labeled anti-cortisol antibody solutions were used, that is, in the case where the same amount of colloidal gold-labeled anti-cortisol antibodies was used. Specifically, the difference between the absorbance of the band that caused by the sample having a cortisol concentration of 242 ng/mL (Experimental Numbers 97 to 105) and the absorbance of the band caused by the sample having a cortisol concentration of 808 ng/mL (Experimental Numbers 106 to 114) when the same volume of the colloidal gold-labeled anti-cortisol antibody solution (the same amount of colloidal gold-labeled anti-cortisol antibodies) was used therefor was calculated.

The difference in the absorbance between a sample having a cortisol concentration of 242 ng/mL (Experimental Numbers 97 to 105) and a sample having a cortisol concentration of 2380 ng/mL (Experimental Numbers 115 to 123) was calculated in the same manner as the above.

Figure 7:
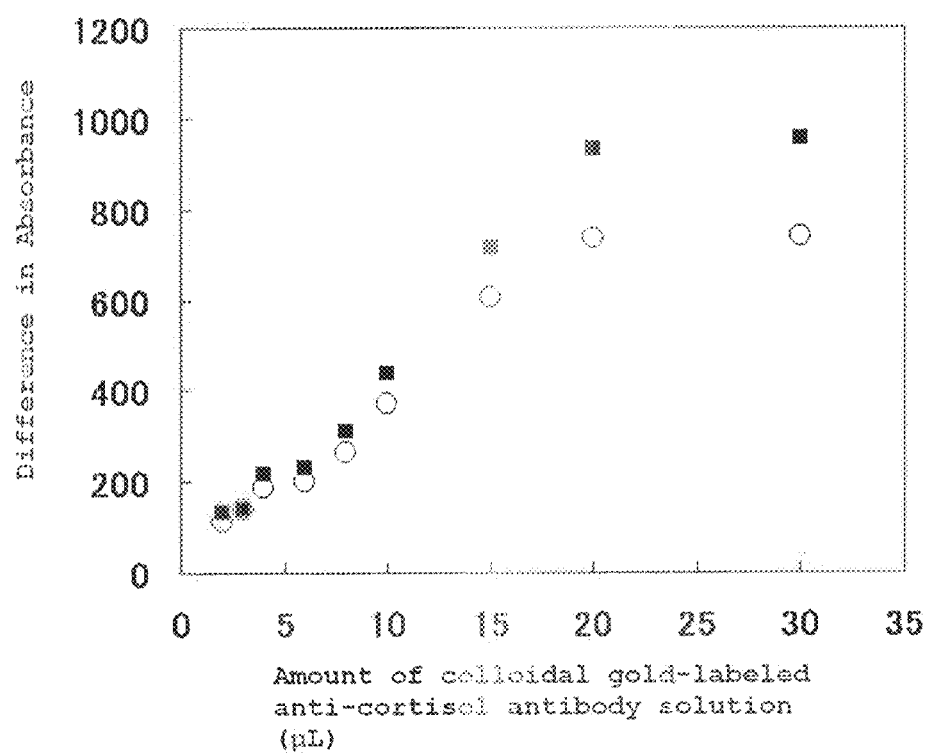
FIG. 7 is a graph showing the relationship between the amount of colloidal gold-labeled anti-cortisol antibody solution and the difference in the absorbance in Test Example 6.
Figure 8:
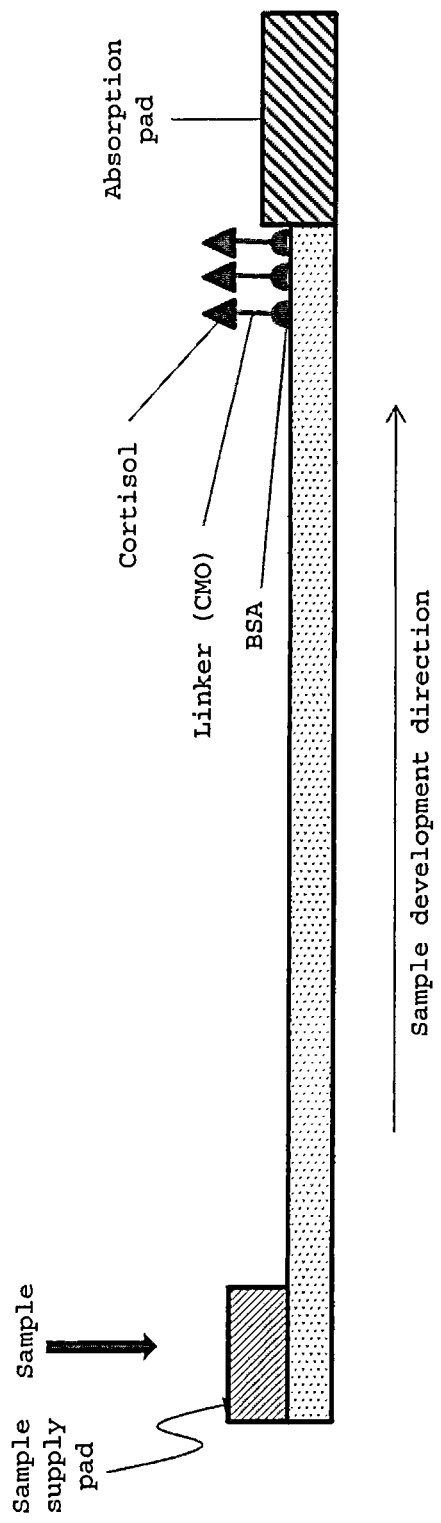
FIG. 8 is an illustration of one embodiment of the immunochromatographic test strip with the location of the sample supply pad, the sample, the cortisol-linker-BSA and the absorption pad with the direction of the sample development indicated.
Figure 9:
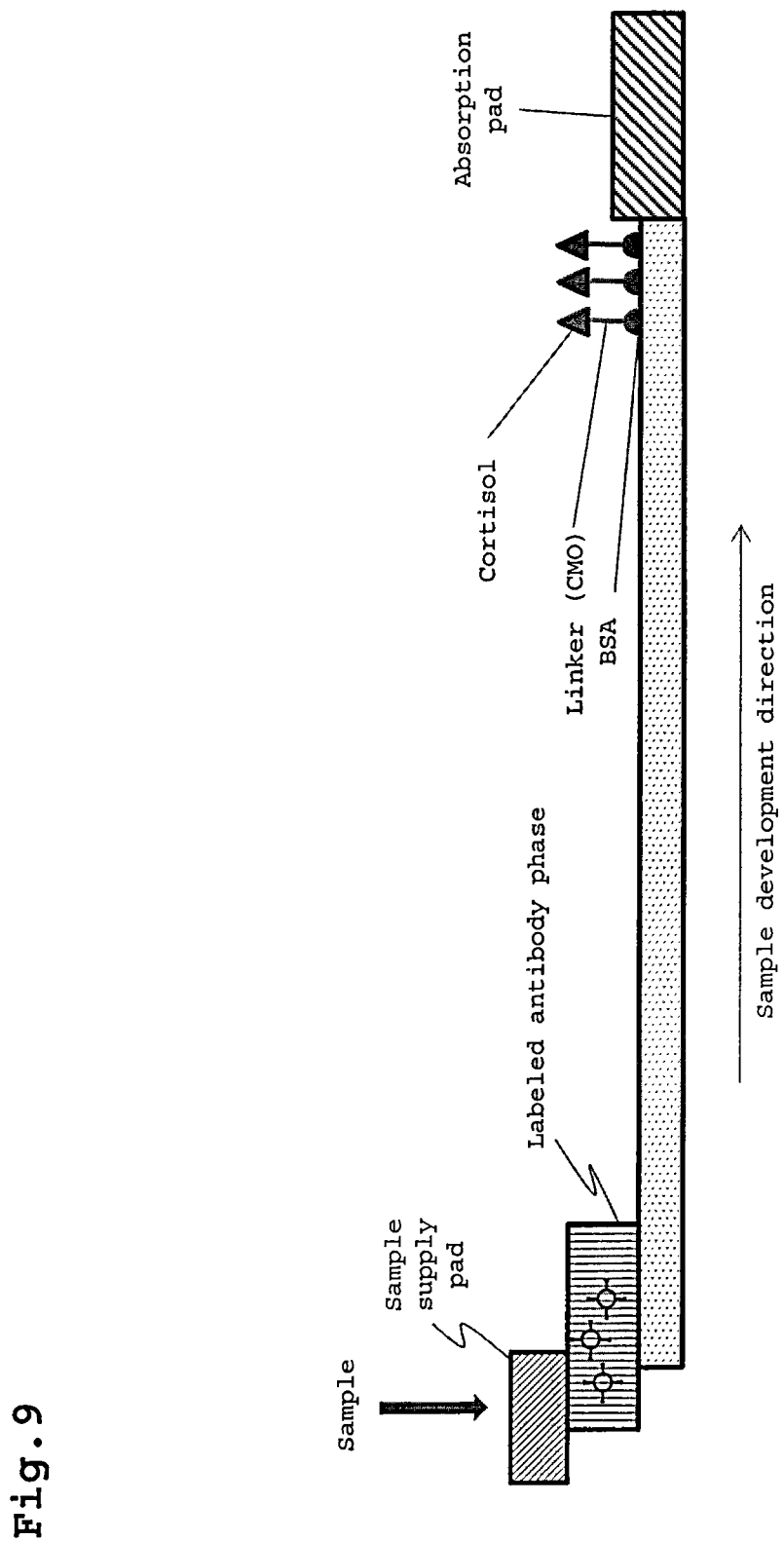
FIG. 9 is an illustration of one embodiment of the immunochromatographic test strip with the location of the sample supply pad, the sample, the labeled antibody phase, the cortisol-linker-BSA and the absorption pad with the direction of the sample development indicated.

The relationship between the amount of the colloidal gold-labeled anti-cortisol antibody solution and the difference in the absorbance is shown in FIG. 7. In FIG. 7, a closed square represents the difference in the absorbance between a sample having a cortisol concentration of 242 ng/mL and a sample having a cortisol concentration of 2380 ng/mL, and an open circle represents the difference in the absorbance between a sample having a cortisol concentration of 242 ng/mL and a sample having a cortisol concentration of 808 ng/mL.

From the results shown in FIG. 7, it can be seen that the more colloidal gold-labeled anti-cortisol antibody solution is increased, that is, the more colloidal gold-labeled anti-cortisol antibodies are increased, the more difference in the absorbance is increased. However, it can be seen that when the amount of the colloidal gold-labeled anti-cortisol antibody solution, that is, the amount of the colloidal gold-labeled anti-cortisol antibody exceeds 20 μL, the difference in the absorbance keeps an almost similar level.

It is preferred that the absorbance on the test line is 200 abs or more when the difference in the absorbance is visually evaluated. Therefore, it can be seen that the difference in the cortisol concentration is easily differentiated by adjusting the amount of the colloidal gold-labeled anti-cortisol antibody solution to 4 to 15 μL when the sample having a high cortisol concentration (cortisol concentration: 200 to 900 ng/mL) is evaluated.

Example 4

(1) Preparation Of an Immunochromatographic Test Strip

A solution obtained by dissolving cortisol-3-O-carboxylmethyl-oxime-BSA (manufactured by Fitzgerald Industries Intl company) in 10 mM phosphate buffer (pH 7.5) so as to have a concentration of 1 mg/mL (hereinafter referred to as "cortisol solution") is applied to a membrane (manufactured by Millipore Corp., trade name: Hi-Flow Plus, 60 mm×4 mm) in line oriented parallel to a narrow side of the membrane. Then, the resulting membrane is dried at room temperature. Thereafter, the membrane is blocked with bovine serum albumin (manufactured by SIGMA Corporation). The portion of cortisol-3-O-carboxylmethyl-oxime-BSA immobilized on the membrane is used as a test line of the immunochromatographic test strip.

A glass fiber conjugated pad in which colloidal gold-labeled cortisol antibody solution has been infiltrated and dried is pasted on a part of one end (hereinafter referred to as "upstream end") of the membrane such that a part of the pad is overlapped to the membrane. Whereby a member (releasing pad) for causing the antigen-antibody reaction of the colloidal gold-labeled anti-cortisol antibodies with cortisol contained in the blood sample to be tested and releasing the mixture of the colloidal gold-labeled anti-cortisol antibodies and the blood sample to be tested to the membrane is provided. A part for holding colloidal gold-labeled anti-cortisol antibodies in the releasing pad is used as a labeled antibody phase. In addition, a sample pad, which is a member for dropping the blood sample to be tested, is pasted on an opposite end of an end of the side in which the membrane has been pasted on the releasing pad such that a part of the sample pad is overlapped thereto.

An absorption pad (manufactured by Millipore Corp., 20 mm×4 mm) is pasted on a downstream end positioned in a longitudinal direction from the applying part of the cortisol solution on the resulting membrane, to give the immunochromatographic test strip.

Next, whether or not cortisol-3-O-carboxylmethyl-oxime-BSA is immobilized on the membrane of the immunochromatographic test strip is evaluated in the same manner as in Example 1. In addition, whether or not the colloidal gold-labeled anti-cortisol antibodies are kept on the releasing pad and whether or not the colloidal gold-labeled anti-cortisol antibodies are developed on the membrane when the blood sample is dropped to the sample pad is evaluated by dropping 10 mM phosphate buffer (pH 7.5) to the sample pad of the immunochromatographic test strip, then keeping the strip to stand, and thereafter confirming the appearance of a red band on the test line.

(2) Evaluation of Blood Sample

A blood sample to be tested is dropped to the sample supply part of the immunochromatographic test strip obtained in Example 4, and thereafter developed on the immunochromatographic test strip. After development, whether or not the blood sample to be tested has a quality suitable for the adrenal vein sampling test can be evaluated on the basis of the amount (absorbance) of the colloidal gold-labeled anti-cortisol antibodies on the test line of the immunochromatographic test strip.

Industrial Applicability

The method for evaluating the quality of a blood sample, the immunochromatographic test strip and the kit for evaluating the quality of a blood sample of the present invention can use for the evaluation of the blood sample for the adrenal vein sampling test and the like. Therefore, these are expected to be utilized in pharmaceutical development, treatment, diagnosis or biochemical research of diseases and the like.

The invention claimed is:

1. An immunochromatographic test strip suitable for determining whether or not a blood sample has a quality suitable for a suprarenal vein sampling test, comprising
   a substrate having two terminal ends in a longitudinal direction;
   a sample supply part on the substrate and positioned-at one terminal end in a longitudinal direction of the substrate;
   an absorption pad on the substrate and positioned on the other terminal end of the substrate in a longitudinal direction of the substrate; and
   cortisol immobilized on the substrate between the sample supply part and the absorption pad and adjacent to the absorption pad,
   wherein the cortisol is immobilized on the substrate via a linker bound to the cortisol and the linker is bound to the substrate of via bovine serum albumin.

2. An immunochromatographic test strip suitable for determining whether or not a blood sample has a quality suitable for a suprarenal vein sampling test, comprising
   a substrate having two terminal ends in a longitudinal direction of the substrate,
   a sample supply part on the substrate at one terminal end in a longitudinal direction of the substrate, the sample supply part comprising a labeled anti-cortisol antibody;
   an absorption pad on the substrate and positioned at the other terminal end in a longitudinal direction of the substrate; and cortisol immobilized on the substrate between the sample supply part and the absorption pad and adjacent to the absorption pad, wherein the cortisol is immobilized to the substrate via a linker bound to the cortisol and the linker is bound to the substrate via bovine serum albumin.

3. A kit for evaluating the quality of a blood sample, comprising the immunochromatographic test strip of claim 1.

4. A kit for evaluating the quality of a blood sample, comprising the immunochromatographic test strip of claim 2.

5. The immunochromatographic test strip according to claim 1, wherein the substrate has a moving speed of 0.22 to 0.45 nm/sec when pure water is provided on the substrate and allowed to move on the substrate.

* * * * *